United States Patent

Ishihara et al.

[11] Patent Number: 6,057,431
[45] Date of Patent: May 2, 2000

[54] AMIDITE DERIVATIVES AND OLIGONUCLEOTIDE DERIVATIVES

[75] Inventors: Hiroshi Ishihara, Ibaraki-Ken; Takayuki Kawaguchi; Masahiro Ikeda, both of Tokyo-To; Kazutaka Nakamoto; Atsushi Sasaki, both of Ibaraki-Ken, all of Japan

[73] Assignee: Drug Delivery System Institute, Ltd., Tokyo, Japan

[21] Appl. No.: 08/930,677

[22] PCT Filed: Mar. 29, 1996

[86] PCT No.: PCT/JP96/00868

§ 371 Date: Dec. 22, 1997

§ 102(e) Date: Dec. 22, 1997

[87] PCT Pub. No.: WO96/30386

PCT Pub. Date: Oct. 3, 1996

[30] Foreign Application Priority Data

Mar. 31, 1995 [JP] Japan .................................. 7-100009

[51] Int. Cl.$^7$ .......................... C07H 21/02; C07H 19/00; C07H 21/00; C07H 1/00
[52] U.S. Cl. ........................ 536/23.1; 536/1.11; 536/4.1; 536/22.1; 536/25.3; 536/25.33; 536/25.34; 435/6; 435/91.1; 435/91.2
[58] Field of Search ............................ 435/6, 91.1, 91.2; 536/22.1, 23.1, 25.3, 1.11, 6.1, 25.33, 25.34

[56] References Cited

FOREIGN PATENT DOCUMENTS 7-502749  3/1995  Japan .

*Primary Examiner*—Jezia Riley
*Attorney, Agent, or Firm*—Wenderoth, Lind & Ponack L.L.P.

[57] ABSTRACT

The present invention provides a compound of general formula (I):

$$X-(CH_2)m-(T^5)r-(CH_2)n-CH\begin{matrix}(CH_2)p-T^3-T^1-F^1\\(CH_2)q-T^4-T^2-F^2\end{matrix} \quad (I)$$

wherein X represents group (II) or (III):

$$Y-P\begin{matrix}O-(CH_2)_2-CN\\|\\O-\end{matrix} \quad (II)$$

$$Z-O-\underset{\underset{O}{\|}}{\overset{\overset{OH}{|}}{P}}-O- \quad (III)$$

wherein Y represents a leaving group and Z represents an oligonucleotide.

The compound can specifically transfer oligonucleotides to cells which specifically recognize a specified saccharide construction. Accordingly, the compound can be used as an antiviral agent or an antitumor agent.

15 Claims, 3 Drawing Sheets

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: Synthetic DNA (iv) ANTI-SENSE: NO (ix) FEATURE:
      (A) NAME/KEY: phosphorotioate (xi) SEQUENCE DESCRIPTION: SEQ ID NO:1:

ATGCCCCTCA ACGTT                                                    15

(2) INFORMATION FOR SEQ ID NO:2:

(i) SEQUENCE CHARACTERISTICS:
      (A) LENGTH: 15 base pairs
      (B) TYPE: nucleic acid
      (C) STRANDEDNESS: single

```
            (D) TOPOLOGY: linear (ii) MOLECULE TYPE: Synthetic DNA (iv) ANTI-SENSE: YES (ix) FEATURE:
            (A) NAME/KEY:phosphorotioate (xi) SEQUENCE DESCRIPTION: SEQ ID NO:2:

AACGTTGAGG GGCAT                                                              15

(2) INFORMATION FOR SEQ ID NO:3:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: Synthetic DNA (iv) ANTI-SENSE: YES (ix) FEATURE:
            (A) NAME/KEY:phosphorotioate (xi) SEQUENCE DESCRIPTION: SEQ ID NO:3:

GGACTCAGAC TCGCGTCC                                                           18
```

AMIDITE DERIVATIVES AND OLIGONUCLEOTIDE DERIVATIVES

This application is a 371 of PCT/JP96/00868 filed Mar. 29, 1996.

BACKGROUND OF THE INVENTION

1. Field of the Invention

The present invention relates to amidite derivatives having a monosaccharide or a derivative thereof at their terminals. In particular, the present invention relates to oligonucleotide derivatives in which oligonucleotides are introduced into said amidite derivatives.

2. Description of the Related Art

In recent years, attempts have been made to suppress the expression of targeted genes using oligonucleotides, specifically antisense oligonucleotides. However, it was found that when administered directly into the body, the oligonucleotides were readily decomposed in the blood, or the greater portion was readily excreted in the urine. Moreover, the nucleotides were decomposed or excreted without being incorporated into the targeted cells of lesioned organs.

To resolve these problems, it has been reported that the formation of a conjugate of asialoorosomucoid with poly-L-lysine yields a complex which ionically interacts with the antisense oligonucleotide of human hepatitis B virus and the ionic complex enhanced the inhibitory effect of the antisence oligodeoxynucleotide on the biosynthesis of viral protein significantly (G. Y. Wu and C. H. Wu (1992) J. Biol. Chem. 267, 12436) and that the chloramphenicol acetyltransferase gene can be transferred into and expressed in the liver using a similar complex (G. Y. Wu and C. H. Wu (1991) Biotherapy 3, 879). Techniques used in these reports are described in WO 93/04701 and 92/20316. Furthermore, it is reported in WO 93/19768 that a complex formed between DNA and a saccharide derivative, which was covalently coupled with a molecule to intercalate into DNA by inserting in the double helix structure (i.e. intercalator) was incorporated into a cell which specifically recognized the saccharide such that it was useful for the efficient expression of genetic information. Nakai et al intravenously injected an antisense nucleic acid complex, and a simulation of the amount delivered into the liver showed that this type of non-covalently bonded complex easily dissociates in the blood to preclude any significant transfer into the liver (D. Nakai, T. Seita and Y. Sugiyama (1995) Pharm. Tech. Japan, 11, 27).

On the other hand, it is known that a compound in which galactose is introduced into carboxymethylated dextran (M. Nishikawa et al. (1993) Pharmaceutical Research 10, 1253), and a compound in which galactose is introduced into poly-L-glutamic acid are selectively distributed in hepatocytes (H. Hirabayashi et al (1994) Proceedings of the General Presentation of the 144th Annual Meeting of Japan Pharmacological Association 30(6) 15-4).

SUMMARY OF THE INVENTION

The present inventors have found that a complex of an oligonucleotide with an amidite derivative having a monosaccharide residue at its terminal is delivered to a specific organ and suppresses expression of a specific gene in cells of the organ. The present invention is based on these findings.

Accordingly, an objective of the present invention is to provide compounds which can incorporate oligonucleotides into organ cells, particularly into hepatocytes.

Another objective of the present invention is to provide amidite derivatives which are useful for synthesis of the compounds.

A compound of the present invention can be represented by general formula (I):

$$X-(CH_2)m-(T^5)r-(CH_2)n-CH\begin{matrix}(CH_2)p-T^3-T^1-F^1\\(CH_2)q-T^4-T^2-F^2\end{matrix} \quad (I)$$

in which
X is group (II):

$$\begin{matrix}O-(CH_2)_2-CN\\|\\Y-P-O-\end{matrix} \quad (II)$$

(in which Y is a leaving group) or group (III):

$$\begin{matrix}OH\\|\\Z-O-P-O-\\\|\\O\end{matrix} \quad (III)$$

(in which Z is an oligonucleotide or its derivative), $T^1$ is $-(CH_2)s-$ (in which s represents an integer between 2 and 10), or $(CH_2CH_2O)t-(CH_2)_2-$ (in which t represents an integer between 1 and 3), $T^2$ is $-(CH_2)u-$ (in which u represents an integer between 2 and 10), $-(CH_2CH_2O)v-(CH_2)_2-$ (in which v represents an integer between 1 and 3), or group (IV):

$$-(CH_2)n^*-CH\begin{matrix}(CH_2)p^*-T^{3*}-T^{1*}-\\(CH_2)q^*-T^{4*}-T^{1**}-F^3\end{matrix} \quad (IV)$$

in which
$T^{1*}$ and $T^{1**}$ are each as defined above for $T^1$, and $n^*$, $p^*$, $q^*$, $T^{3*}$, $T^{4*}$ and $F^3$ are each as defined below for n, p, q, $T^3$, $T^4$ and $F^1$, where each group and its asterisk-labeled counterpart can be the same or different, $T^3$, $T^4$ and $T^5$, which may be the same or different, each represent —CONH—, —NHCO— or —O—, provided that when either one of $T^3$, $T^4$ and $T^5$ represents —O—, other two groups represent a group other than —O—, $F^1$ and $F^2$, which may be the same or different, each represent a monosaccharide selected from the group consisting of galactose, glucose and galactosamine, or a derivative thereof, or a disaccharide consisting of the monosaccharide and/or the derivative thereof, wherein a hydroxyl group (s) which does not participate in any reactions in the monosaccharide, the derivative thereof and the disaccharide can be protected, m represents an integer between 0 and 10,
n represents an integer between 0 and 4,
p represents an integer between 0 and 4, q represents an integer between 0 and 4 and
r represents an integer 0 or 1.

Lanes 1 and 8 are with no compound, Lanes 2–4 are with the compound of Example 19 (2), and Lanes 5–7 are with the compound of Example 19 (1). The compounds were added at a concentration of 0.04 μM for the compounds of Lanes 2 and 5, 0.20 μM for the compounds of Lanes 3 and 6 and 1 μM for the compounds of Lanes 4 and 7.

Figure 3:
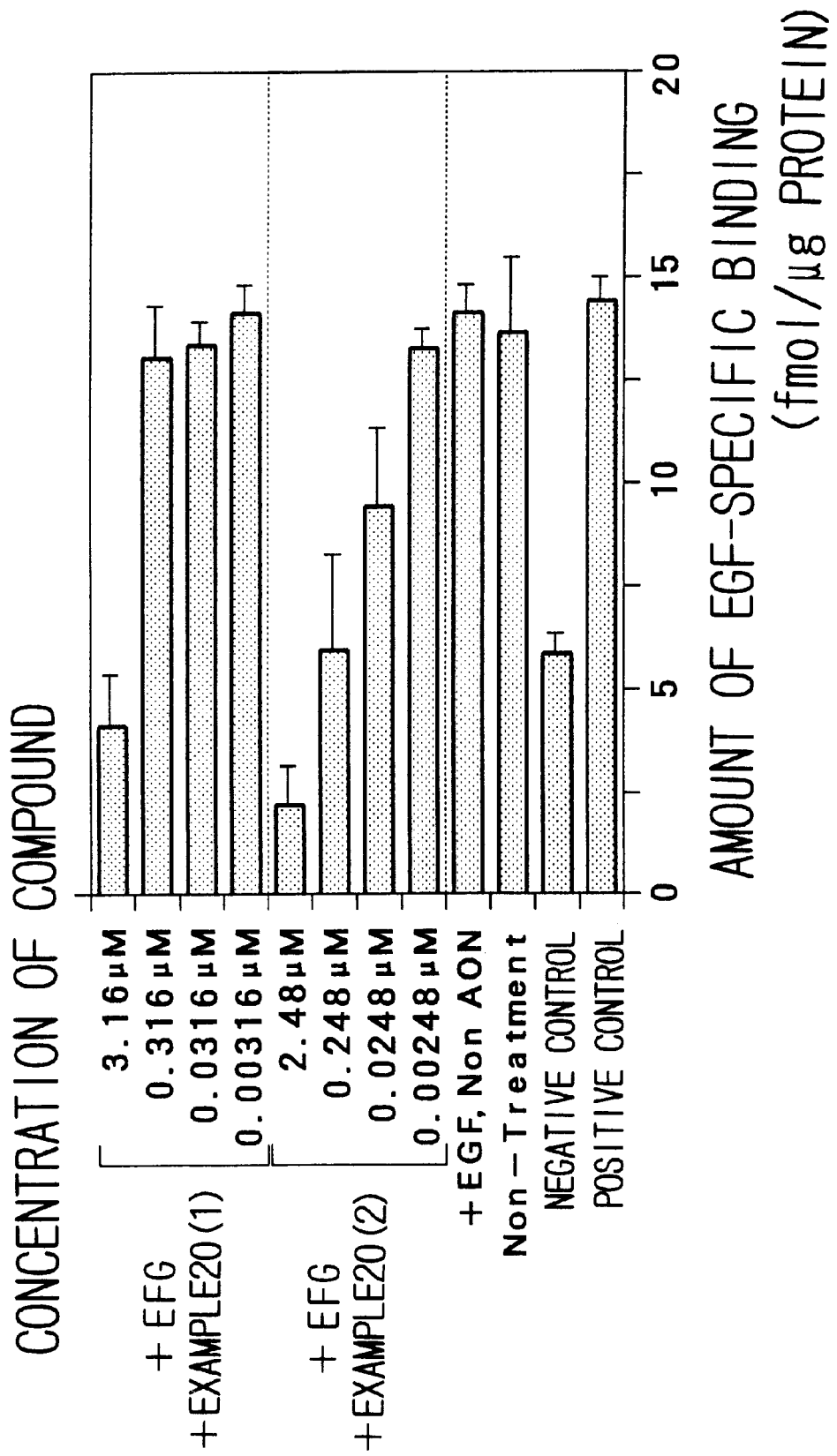

FIG. 3 shows the effect of compounds of the present invention (Examples 20 (1) and (2)) on down regulation of epidermal growth factor receptors in a primary culture of hepatocytes isolated from rats.

Figure 4:
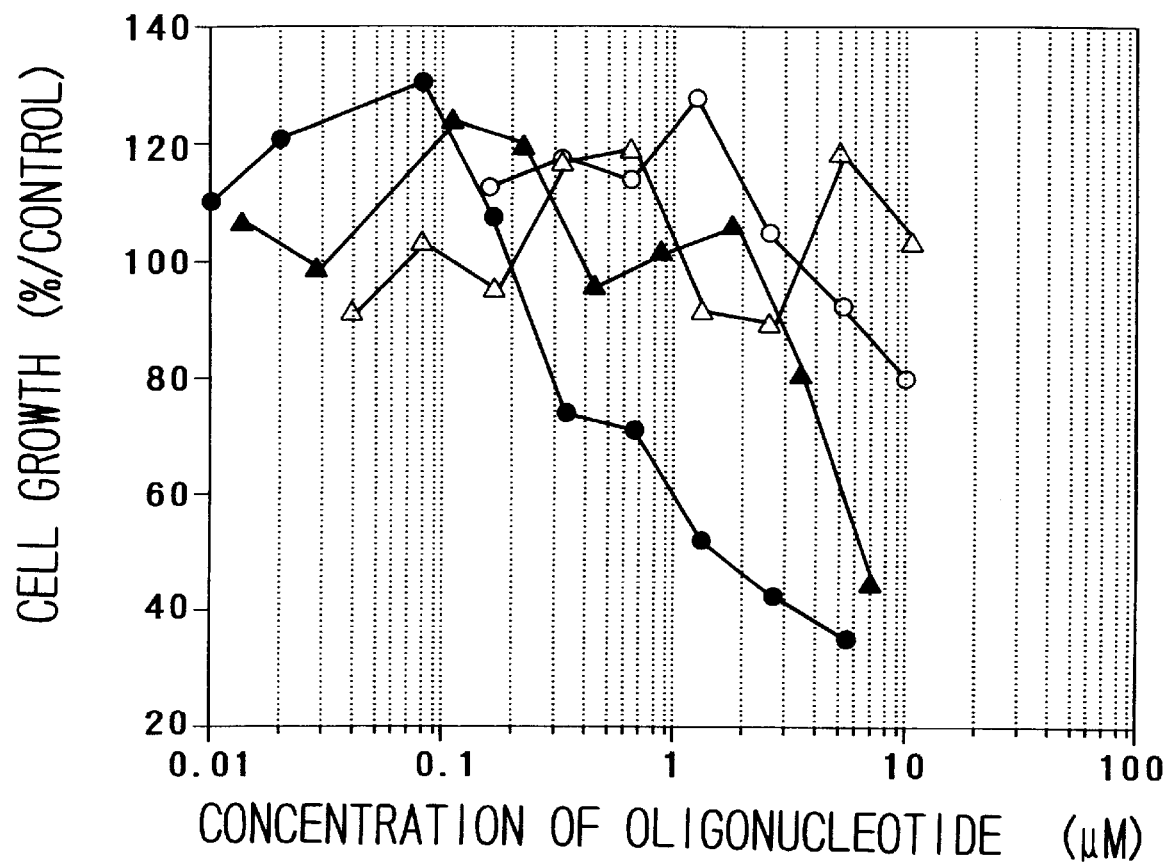

FIG. 4 shows the effect of compounds of the present invention on growth of HepG2 cells. Black circles, black triangles, white circles and white triangles are with compounds of Example 19 (2), Example 19 (1), Example 18 (2) and Example 18 (1), respectively.

DESCRIPTION OF THE PREFERRED EMBODIMENTS

Compounds of general formula (I)

In general formula (I), $F^1$, $F^2$ and $F^3$ are a monosaccharide selected from the group consisting of galactose, glucose and galactosamine, preferably galactose or galactosamine. The monosaccharide may be a derivative thereof. Examples of such derivative include an N- or O-acyl derivative (e.g., N-acetylgalactosamine), an O-alkyl derivative including carboxyalkyl derivatives (e.g., carboxymethyl derivatives), and an ester derivative with acids such as sulfuric acid, phosphoric acid and carboxylic acid (e.g., sulfate ester derivatives), preferably N-acetylgalactosamine.

$F^1$, $F^2$ and $F^3$ may also be a disaccharide consisting of the monosaccharide and/or the monosaccharide derivative. Preferable examples of such disaccharide include those having galactose, galactosamine or N-acetylgalactosamine at the non-reducible end, and are preferably lactose, lactosamine and N-acetyllactosamine.

In the present invention, the hydroxyl group of the monosaccharide and the derivative thereof and the disaccharide which do not participate in any reactions can be protected. Examples of such protecting group include an acyl group, preferably a straight chain or branched $C_{1-6}$ (preferably $C_{1-4}$) alkylcarbonyl group, more preferably an acetyl group. Furthermore, in general formula (I), when group X is group (II), it is preferable that non-reacting hydroxyl groups be protected, and when group X is group (III), it is preferable that non-reacting hydroxyl groups not be protected.

The monosaccharide and the derivative thereof and the disaccharide herein mean a saccharide in which one of the hydrogen atom(s) of the hydroxyl group(s) (preferably a hydroxyl group in an anomer position) in the saccharide molecule is removed. In this case, bonds between $F^1$, $F^2$ and $F^3$ and $T^1$, $T^2$ and $T^{1**}$ can be either an α-glycosidic linkage or a β-glycosidic linkage.

In $T^1$ and $T^2$, s and u are integers between 2 and 10, preferably between 2 and 8, and t and v are integers between 1 and 3, preferably 2.

The compounds of the present invention may have a group (IV) described above in $T^2$ of general formula (I). The group represented by general formula (IV) has substantially the same meaning as that represented by general formula (I) without X—(CH$_2$)m—(T$^5$)r— and —F$^2$. Accordingly, $T^{1*}$ and $T^{1**}$ are as defined in $T^1$, and may be the same as or different from $T^1$. Furthermore, n*, p* and q* are integers in the range as defined in n, p and q and may be the same as or different from n, p and q. Furthermore, $T^{3*}$, $T^{4*}$ and $F^3$ are as defined in $T^3$, $T^4$ and $F^1$ and may be the same as or different from $T^3$, $T^4$ and $F^1$.

In general formula (I), $T^3$, $T^4$ and $T^5$, which may be the same or different, each independently represent —CONH—, —NHCO— or —O—, preferably —CONH—. Further, when one of $T^3$, $T^4$ and $T^5$ is —O—, the remaining two are not —O—.

In general formula (I):

m is an integer between 0 and 10, preferably 0 or between 2 and 10, more preferably between 3 and 9, n is an integer between 0 and 4, preferably 0, 1 or 2, more preferably 0, p is an integer between 0 and 4, preferably 0, 1 or 2, more preferably 0, q is an integer between 0 and 4, preferably 1 or 2, more preferably 2, and r is an integer 0 or 1, more preferably 1.

When r is 0, —(T$^5$)r— is a bond.

Examples of leaving groups represented by Y in group (II) include a diisopropylamino group and a morpholyl group (preferably morpholyl-4-yl group).

Examples of oligonucleotides represented by Z in group (III) include an oligodeoxyribonucleotide (DNA) and an oligoribonucleotide (RNA). Furthermore, their sequences and number of bases are not limited and can be appropriately determined according to the use of the compounds.

Examples of nucleotide derivatives include those in which one or two of the oxygen atoms at a phosphoric ester bonding site are substituted by other atoms or groups as shown by the following formula:

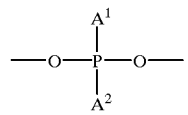

Combinations of $A^1$ and $A^2$ and names of the resulting derivatives are as follows:

TABLE 1

Combination of $A^1$ and $A^2$ and names of derivatives

| $A^1$ | $A^2$ | Name of derivative |
| --- | --- | --- |
| —OH | =O | Phosphodiester (natural type) |
| =O | —CH$_3$ | Methyl phosphonate |
| —OH | =S | Phosphorothioate |
| —SH | =S | Phosphorodithioate |
| =O | —O—R | Alkylphosphotriester |
| =S | —CH$_3$ | Methylphosphonothioate |
| =O | —NH—R | Alkylphosphoramidite |
| =O | —BH$_3$ | Boranophosnate |

In the table, R represents an alkyl group.

Further, substitution may occurred at all or a part of the phosphoric ester bonds in the nucleotides and substitution may occurred at an atom(s) or group(s) in each phosphoric ester bond.

Examples of oligonucleotide derivatives which can be easily synthesized include natural phosphodiesters and phosphorothioate derivatives.

Oligonucleotides represented by Z can be antisense oligonucleotides. Examples of antisense oligonucleotides include those which have antiviral activity, in particular, an antisense oligonucleotide against the surface antigen of hepatitis B virus (HBsAg) (Goodarzi, G. at al (1990) J. Gen. Virol. 71, 3021) and an antisense oligonucleotide against the envelope protein of hepatitis B virus (HBeAg) (Blum, H. E. et al (1991) Lancet 337, 1230). Other examples include (2'-5')oligoadenylate which is known to be responsible for the antiviral activity of interferon and those which suppress expression of cancer genes.

Examples of oligonucleotides represented by Z include DNA sequences shown in SEQ ID Nos: 1 to 3.

The sequence of SEQ ID No: 1 is a 15 mer oligodeoxynucleotide (sense sequence) having a sequence identical to the base sequence of 5 codons starting from the translation start codon toward the 3' end of messenger RNA derived from the human c-myc gene. The sequence of SEQ ID No: 2 is a 15 mer oligodeoxynucleotide (antisense sequence) having a sequence complementary to the base sequence of 5 codons starting from the translation start codon toward the 3' end of messenger RNA derived from the human c-myc gene. The sequence of SEQ ID No: 3 is a 18 mer oligodeoxynucleotide (antisense sequence) having a sequence complimentary to the sequence between the 33th and the 50th from the 3' end of messenger RNA derived from the rat epidermal growth factor receptor protein.

A group of preferable compounds according to the present invention include compounds of formula (I), in which $T^1$ is —$(CH_2)_s$— (in which s represents an integer between 2 and 8) or —$(CH_2CH_2O)_2$—$(CH_2)_2$—, $T^2$ is —$(CH_2)_u$— (in which u represents an integer between 2 and 8), —$(CH_2CH_2O)_2$—$(CH_2)_2$—, or group (IV) (in which $T^{1*}$ and $T^{1**}$ are as defined for $T^1$ but each can be the same as or different from $T^1$, and $n^*, p^*, q^*, T^{3*}, T^{4*}$ and $F^3$ are as defined thereinafter for $n, p, q, T^3, T^4$ and $F^1$, but can be the same as or different from $n, p, q, T^3, T^4$ and $F^1$, respectively), $T^3, T^4$ and $T^5$ are —CONH—, $F^1$ and $F^2$, which may be the same or different, each represent galactose, galactosamine, N-acetylgalactosamine, lactose, lactosamine or N-acetyllactosamine, m is an integer 0 or between 2 and 10, n is an integer 0, 1 or 2.

P is an integer 0, 1 or 2, q is an integer 0, 1 or 2, and r is an integer 1.

More preferable compounds according to the present invention are compounds expressed by general formula (Ia):

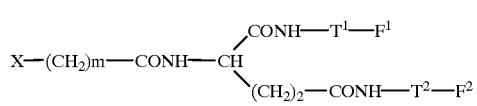

(Ia)

in which

X is group (II):

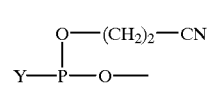

(II)

(in which Y is a leaving group)
or group (III)

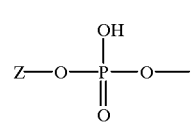

(III)

(in which z is an oligonucleotide or a derivative thereof) $T^1$ is —$(CH_2)_s$— (in which s represents an integer between 2 and 8) or —$(CH_2CH_2O)_2$—$(CH_2)_2$—, $T^2$ is —$(CH_2)_u$— (in which u represents an integer between 2 and 8), —$(CH_2CH_2O)_2$—$(CH_2)_2$—, or group (IVa):

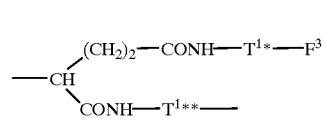

(IVa)

in which $T^{1*}$ and $T^{1**}$ are as defined for $T^1$, and $F^3$ is as defined thereinafter for $F^1$, but can be the same as or different from $T^1$ and $F^1$ respectively, and $F^1$ and $F^2$, which may be the same or different, each represent a monosaccharide selected from the group consisting of galactose and galactosamine, or a derivative thereof, or a disaccharide consisting of the monosaccharide and/or the derivative thereof, wherein a hydroxyl group(s) which does not participate in any reactions in the monosaccharide, the derivative thereof and the disaccharide can be protected, and m is an integer between 3 and 9.

The compounds of the present invention have a monosaccharide or a derivative thereof at their terminals. Accordingly, the compounds of the present invention can deliver a specified sugar structure to cells which specifically recognize it.

Preparation of Compounds of General Formula (I)

The compounds of general formula (I) in which group X is not group (II) or group (III) but a hydroxyl group can be obtained by one of the following method (1), (2) or (3): (1) A compound of formula (V):

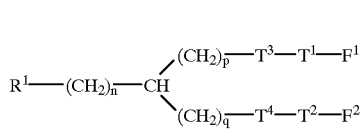

(V)

(in which $R^1$ is a halogen atom, a protected or unprotected hydroxyl group, amino group or carboxyl group, $T^{1-4}, F^1, F^2, n, p$ and q are as defined above, but functional groups not involved in any reactions of $F^1$ and $F^2$ are preferably protected)

may be reacted with the compound of formula (VI):

  (VI)

(in which $R^1$ is as defined above, $R^2$ is a protected or unprotected hydroxyl group, and m is as defined above) as follows: to form an amide bond, by a condensation method in the presence of a condensation agent (e.g., dicyclohexylcarbodiimide), by reaction with a mixed acid anhydride in the presence of isobutyl chlorocarbonate or the like, or by reaction with an active ester using hydroxysuccinimide or the like; alternatively to form an ether bond, by a condensation reaction between a corresponding halogen compound and alkoxide. In either case, the usual reaction temperatures and reaction times for the respective method can be applied.

The compound of formula (V) above can be obtained by reacting a compound of formula:

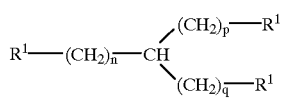  (VII)

(in which $R^1$, n, p and q are as defined above) with a compound of formula (VIII):

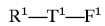  (VIII)

(in which $R^1$, $T^1$ and $F^1$ are as defined above) by a condensation reaction or the like as described above, followed by deprotection if necessary. Further, a compound of formula (V) in which $T^2$ is represented by group (IV) can be obtained by reacting (e.g., condensation) two of the same or two different compounds of formula (VII), occasionally followed by deprotection if necessary, then by reacting the intermediate with a compound of formula (VIII).

(2) A compound of formula (IX):

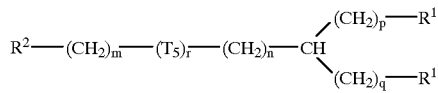  (IX)

(in which $R^1$, $R^2$, $T^5$, m, n, p and q are as defined above) and a compound of formula (VIII) are reacted by a condensation reaction or the like as described above, occasionally followed by deprotection if necessary, to obtain the target compound.

The compound of formula (IX) can be obtained by reacting a compound of formula (VII) with a compound of formula (VI) by a condensation reaction or the like as described above, followed by deprotection if necessary. Further, a compound of formula (I) in which $T^2$ is represented by group (IV) can be obtained by reacting a compound of formula (VII) with a compound of formula (IX) by a condensation reaction or the like as described above, followed by deprotection if necessary, and then reacting the intermediate with a compound of formula (VIII).

(3) A compound of formula (X):

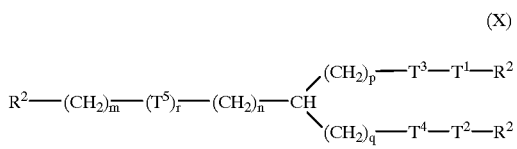  (X)

(in which $R^{1-5}$, $R^2$, m, n, p, q and r are as defined above) and a compound of formula (XI):

  (XI)

(in which D is a halogen atom, an acyloxy group (e.g., acetoxy group) or $CCl_3C(=NH)O—$, and $F^*$ is $F^1$ or $F^2$) are glycosylated at a reaction temperature between $-20°$ C. and room temperature for 10 minutes to 24 hours, followed by deprotection if necessary, to obtain the target compound.

The compound of formula (X) above can be obtained by reacting a compound of formula (IX) with a compound of formula (XII):

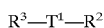  (XII)

(in which $R^2$, $R^3$ and $T^1$ are as defined above) by a condensation reaction or the like as described above, followed by deprotection if necessary.

A compound of general formula (I) in which group X is group (II) can be obtained by reacting a compound of general formula (I) in which group X is a hydroxyl group with a compound of formula (XIII):

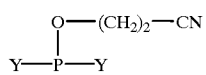  (XIII)

(in which Y is a leaving group) in the presence of an activating reagent (e.g., tetrazole) at a reaction temperature between $-20°$ C. and room temperature for 10 minutes to several hours.

A compound of general formula (I) in which group X is group (III) can be obtained by reacting a compound of general formula (I) in which group X is group (II) with a nucleotide using an ordinary DNA synthesis method such as the β-cyanoethylphosphoramidite method.

In the β-cyanoethylphosphoramidite method, nucleotides are first immobilized on a solid phase, then coupled with an amidite monomer (in which hydroxyl groups not involved in bonding are preferably protected) activated by an activating agent such as tetrazole, oxidized with an oxidizing agent (e.g., an aqueous iodine solution), and cleaved from the solid phase, and deprotection if necessary. Natural phosphodiester-type oligonucleotides to be immobilized on a solid phase can be obtained in advance by repeating this reaction.

Furthermore, phosphorothioate-type oligonucleotides can be synthesized using a reagent which can generate free sulphur atoms in an oxidation reaction (e.g., Beaucage reagent).

Furthermore, various phosphoric ester bonds can be formed using amidites in which oxygen atoms at phosphoric acid sites are substituted by various functional groups. For example, a phosphorodithioate-type oligonucleotide can be obtained by oxidizing with sulphur atoms using 5'-dimethoxytrityldeoxynucleoside 3'-(dimethylamino) phosphorothioamidite (W. K. D. Bill et al (1989) J. Am.

Chem. Soc. 111, 2321). Furthermore, a methylphosphonate-type phosphoric ester bond can be formed using 5'-methoxytrityldeoxynucleoside 3'-methylphosphonate and mesitylenesulfonyl-3-nitrotriazole (P. S. Miller et al (1983) Nucleic Acid Res. 11, 6225). Furthermore, an ethylphosphotriester-type phosphoric ester bond can be formed using 5'-dimethoxytrityldeoxynucleoside 3'-O-ethyl-N,N-diisopropylphosphoramidite (K. A. Gallo et al (1986) Nucleic Acid Res. 14, 7405).

The compounds so synthesized are purified by partition chromatography (e.g., octadecyl silica gel column chromatography), ion-exchange chromatography (e.g., anion-exchange column chromatography), affinity chromatography (e.g., RCA lectin affinity chromatography) or the like.

Use of Compounds/Pharmaceutical Compositions

The compounds of the present invention have a monosaccharide or a derivative thereof at their terminals. Therefore, the compounds of the present invention can be delivered specifically to cells which recognize a specified sugar structure. Furthermore, the compounds of the present invention can have an oligonucleotide or a derivative thereof at their terminals. This oligonucleotide can be one which can suppress expression of a specified gene in cells of a targeted organ, for example, an antisense oligonucleotide. Accordingly, the compounds of the present invention can be used as therapeutic agents for various diseases.

The compounds of the present invention can deliver an antisense oligonucleotide which is effective as an anti-viral agent to hepatic cells infected with viruses to enhance anti-viral activity. Furthermore, the compounds of the present invention can deliver an antisense oligonucleotide which is effective as an anti-malignant tumor agent to cancerous hepatic cells to enhance anticancer activity.

Another aspect of the present invention is to provide pharmaceutical compositions comprising the compound of the present invention together with pharmaceutically acceptable carriers.

Thus, the pharmaceutical compositions can be used as a therapeutic agent for malignant tumors (e.g., a therapeutic agent for cancers), an anti-viral agent, an antirheumatic agent (e.g., an agent to suppress production of tumor necrosis factor), an anti-inflammatory agent, an anti-allergy agent or an immunosuppressive agent (e.g., an agent to inhibit migration of immunocompetent cells to inflammatory sites), an agent to improve circular functions (e.g., agents to inhibit growth of vascular smooth cells associated with re-obstruction of coronary vessels), an agent to improve endocrine functions (e.g., agents to inhibit abnormal hormone secretion), or a therapeutic agent for diseases which are caused by abnormal expression or functional abnormality of specific proteins and of which symptoms can be improved by suppressing expression of the proteins (e.g., an agent to suppress abnormal expression of receptor proteins of cells).

If the pharmaceutical composition is a therapeutic agent for malignant tumors, Z in formula (I) can be an antisense oligonucleotide to suppress expression of cancer genes. If the pharmaceutical composition is an anti-viral agent, Z in formula (I) can be an antisense oligonucleotide having antiviral activity.

A pharmaceutical composition of the present invention can be administered to human and other animals either orally or non-orally (e.g., intravenous and intramuscular injection, and subcutaneous, rectal, endermic and nasal administration).

The compounds of the present invention can be prepared into suitable dosage form depending on their use, such as tablets, capsules, granules, powders, pills, grains and troches for oral administration, injectable solutions for intravenous or intramuscular injections, formulations for rectal administration, oily suppositories and water-soluble suppositories. These various pharmaceutical preparations can be prepared by ordinary methods using customary excipients, bulking agents, binders, wetting agents, disintegrating agents, surfactants, lubricating agents, dispersing agents, buffering agents, preservatives, solubilizing agents, antiseptics, flavor/odor controlling agents, analgesic agents, stabilizers or the like. Examples of the nontoxic additives to be used include lactose, fructose, glucose, starch, gelatin, magnesium carbonate, synthetic magnesium silicate, talc, magnesium stearate, methylcellulose, carboxymethyl cellulose or salts thereof, gum arabic, polyethylene glycol, syrup, vaseline, glycerin, ethanol, propylene glycol, citric acid, sodium chloride, sodium sulfite and sodium phosphate. If necessary, effective components other than the compounds of the present invention can be added.

The particular dose for each individual patient is determined as a function of usage, age and sex of the patient and severity of symptoms; however, a daily dose for an adult is generally between about 0.05 and 250 mg, preferably between about 0.5 and 50 mg, which can be administered as a single dose or divided into several doses.

In this specification, the term "therapy" means both the treatment and the prevention of diseases.

Another aspect of the present invention is to provide a method for treating a disease selected from the group consisting of a malignant tumor, a viral infection, an inflammatory disease, an allergic disease, an immune disease, a circulatory disease and an endocrine disease comprising administrating the compound of the present invention to an animal (e.g., a mammal) including a human.

Another aspect of the present invention is to provide use of the compound of the present invention for manufacturing a medicament selected from the group consisting of a therapeutic agent for malignant tumors, an anti-viral agent, an antirheumatic agent, an anti-inflammatory agent, an anti-allergic agent, an immunosuppressive agent, an agent to improve circulatory functions and an agent to improve endocrine functions, and use of the compound of the present invention for a medicament selected from the group consisting of a therapeutic agent for malignant tumors, an anti-viral agent, an antirheumatic agent, an anti-inflammatory agent, an anti-allergic agent, an immunosuppressive agent, an agent to improve circulatory functions and an agent to improve endocrine functions.

EXAMPLES

The present invention will be explained by the following examples; however, the invention is not intended to be limited to these examples.

The following abbreviations are used: Boc: benzyloxycarbonyl group, THF: tetrahydrofuran, DMF: dimethylformamide, EDC: 1-(3-dimethylaminopropyl)-3-ethylcarbodiimide, DMAP: 4-dimethylaminopyridine, TLC: thin layer chromatography, DMT group: dimethyltrityl group, TEAA: triethylammonium acetate, ODS column: octadecyl silica gel column.

Synthesis Example 1

Synthesis of Boc-L-glutamyl-L-glutamic acid α',α,γ-tribenzyl ester 15 g (45 mmol) of Boc-L-glutamic acid α-benzyl ester and 455 g (45 mmol) of N-methylmorpholine were mixed and dissolved in 300 ml of dry THF, and the resulting solution was cooled and stirred on a dry ice/acetone bath under a nitrogen gas flow. To this solution, a dry THF solution containing 1 equivalent of ethyl chloroformate (4.89 g/10 ml) was added dropwise for about 5 minutes, and the resulting reaction solution was stirred at −30° C. for 1 minute. The solution was again cooled on a dry ice/acetone bath and stirred, and a dry DMF solution containing 1 equivalent of L-glutamic acid dibenzyl ester tosylate and N-methylmorpholine (22.5 g and 4.55 g/50 ml, respectively) were added dropwise. The solution was stirred at a temperature between −40 and −20° C. for 1 hour and then at a temperature between −20 and 10° C. for 1 hour to complete the reaction. Insoluble matter was removed by filtration using Celite. After concentrating the solvents, the concentrate was dissolved by adding ether (400 ml). The resulting ether solution was washed consecutively with 5% citric acid, an aqueous saturated sodium bicarbonate solution and an aqueous saturated sodium chloride solution. After drying on magnesium sulphate and concentrating under vacuum, the resulting residue was crystallized in isopropyl ether. Next, the resulting crystals were filtered and dried under vacuum to obtain 27.90 g of the title compound as a white powder.

Yield: 95.9%, mp=92–93° C. $[\alpha]_D$=−25.8 (C=1.06, 24° C., methanol)

Synthesis Example 2
Synthesis of N-(10-hydroxydecanoyl)-L-glutamyl-L-glutamic acid α',α,γ-tribenzyl ester (1) Synthesis of 10-hydroxysuccinimidyl decanoate active ester 7.53 g (40 mmol) of 10-hydroxydecanoic acid and 11.5 g (100 mmol) of N-hydroxysuccinimide were dissolved in 80 ml of dry DMF, and 19.0 g (0.1 mol) of EDC was added while stirring at room temperature. After stirring at room temperature overnight, the resulting reaction solution was concentrated under vacuum. Cold water was added to the concentrated residue, and the admixture was stirred and then centrifuged. The resulting precipitate was washed with cold water (150 ml×2) and then dissolved in chloroform. The resulting solution was dried on magnesium sulphate and concentrated under vacuum. 7.57 g of 10-hydroxysuccinimidyl decanoate was obtained as a white powder.

Yield: 66.3%. NMR (500 MHz in CDCl$_3$): $\delta_{TMS}$= 1.24–1.46 (9H, m, —(CH$_2$)$_4$—, and OH), 1.5–1.6 (4H, m, —(CH$_2$)$_4$—), 1.75 (2H, quintet, J=7.5 Hz, —CH$_2$—CH$_2$—CO$_2$Su), 2.60 (2H, t, J=7.5 Hz, —CH$_2$—CO$_2$Su), 2.76–2.94 (4H, m, —(CH$_2$)$_2$— on Su), 3.64 (2H, t, J=6.5 Hz, —CH$_2$—OH); IR(KBr): vcm$^{-1}$=3440(OH), 1820(COOSu), 1790, 1740, 1730

(2) Synthesis of N-(10-hydroxydecanoyl)-L-glutamyl-L-glutamic acid α',α, γ-tribenzyl ester 6.47 g (10 mmol) of the compound obtained in Synthesis Example 1 were dissolved in 50 ml of dry methylene chloride, and 15 ml of trifluoroacetic acid were added while cooled in an ice-ethanol bath. After stirring at room temperature for 1 hour and concentrating under vacuum, the resulting residue was dissolved in an aqueous saturated sodium bicarbonate-chloroform mixed solution (40 ml–100 ml). After extracting with chloroform, the organic layer was washed with an aqueous saturated sodium chloride solution, dried on magnesium sulphate, and concentrated under vacuum. 0.1 g of DMAP and dry acetonitrile (50 ml) was added immediately to dissolve the concentrated residue. The admixture was stirred while cooled in an ice bath, a dry acetonitrile solution containing 4.28 g (15 mmol) of 10-hydroxysuccinimidyl decanoate (20 ml) was added, and the reaction was carried out overnight. 10 ml of an aqueous saturated sodium bicarbonate solution were added. The admixture was stirred for 20 minutes and then concentrated under vacuum. The resulting residue was dissolved in 50 ml of chloroform and washed consecutively with an aqueous saturated sodium bicarbonate solution (30 ml) and an aqueous saturated sodium chloride solution (30 ml×2). After drying on magnesium sulphate and concentrating under vacuum, the resulting residue was purified on silica gel column chromatography (150 g, chloroform:ethyl acetate= 4:1) to obtain 5.22 g of the title compound as a white powder.

Yield: 71.8%, mp=86–88° C.; $[\alpha]_D$=−22.2 (C=0.98, 25° C., methanol); NMR (500 MHz, in CDCl$_3$): $\delta_{TMS}$=1.20–1.38 (10H brm, —(CH$_2$)$_5$—, on decanoic acid), 1.50–1.65 (7H, m, —(CH$_2$)$_3$— on decanoyl and OH), 1.90–2.07 (2H, m, β-CH$_2$ on Glu×½×2), 2.12–2.28 (6H, m, β-CH$_2$ on Glu½× 2, —CH$_2$—CO on dedanoyl and γ-CH$_2$ on Glu×½×2), 3.62 (2H, q, J=6.5 Hz, CH$_2$OH), 5.04–5.22 (6H, m, PhCH$_2$O×3), 6.48 (1H, d, J=7.5 Hz, NH on Glu), 6.52 (1H, d, J=7.5 Hz, NH on Glu), 7.24–7.42 (15H, m, C$_6$H$_5$×3); IR(nujol): vcm$^{-1}$=3290(OH), 1740(COOSu), 1640(CONHCO); FAB-MS:m$^+$/z=717(M+H$^+$)

Synthesis Example 3
Synthesis of N-(4-benzyloxybutynoyl)-L-glutamyl-L-glutamic acid α',α,γ-tribenzyl ester (1) Synthesis of 4-benzyloxybutyric acid 4.0 g (60%, 0.1 mol) of sodium hydride were washed in hexane and mixed with 30 ml of dry DMSO, and the resulting admixture was stirred at 60° C. on an oil bath for 1 hour under a nitrogen gas flow. The mixture was stirred at room temperature, and dry DMSO containing 12.6 g (0.1 mol) of sodium 4-hydroxybutyrate (100 ml) was added. After stirring at room temperature for 2 hours, the reaction solution was cooled on an ice bath, 0.2 mol of benzyl bromide was added, and the reaction was carried out at room temperature for 2 hours. After solidification, 0.5 L of ether was added, the admixture was filtered, the resulting residue was washed with ether (300 ml×3), and the filtrate was concentrated under vacuum. The resulting residue was mixed with 100 ml of methanol, 100 ml of 8% sodium hydroxide were added, and the admixture was stirred at 60° C. for 15 hours. After drying under vacuum, the resulting concentrated residue was washed with ether (200 ml×2), and the ether layer was extracted with 1 N sodium hydroxide (50 ml). All aqueous layers were combined, neutralized with concentrated hydrochloric acid (pH<4) and then extracted with ether (100 ml×5). The ether layer was extracted with 2 N sodium hydroxide (50 ml×3), all water layers were neutralized with concentrated hydrochloric acid (pH<4), and further extracted with ether. The resulting product was washed with an aqueous saturated sodium chloride solution, dried on magnesium sulphate, and then concentrated under vacuum. 9.42 g of 4-benzyloxybutyric acid was obtained as a pale yellow oil.

Yield: 49.5%. NMR (500 MHz, in CDCl$_3$): $\delta_{TMS}$=1.95 (2H, dt, J=6 and 7 Hz, β-CH$_2$), 2.50 (2H, t, J=7 Hz, α-CH$_2$), 3.54 (2H, t, J=6 Hz, γ-CH$_2$), 4.52 (2H, s, PhCH$_2$O), 7.25–7.4 (5H, m, C$_6$H$_5$), 10.0–10.8 (1H, br, CO$_2$H); IR (neat): vcm$^{-1}$=1710(COOH); FAB-MS:m$^+$/z=195(M+H$^+$)

(2) Synthesis of N-(4-benzyloxybutyroyl)-L-glutamyl-L-glutamic acid α',α,γ-tribenzyl ester 6.47 g (10 mmol) of the compound obtained in Synthesis Example 1 were dissolved in 50 ml of dry methylene chloride, and 15 ml of trifluoroacetic acid were added while cooled in an ice-ethanol bath. After stirring at room temperature for 1 hour and concentrating under vacuum, the resulting residue was dissolved in an aqueous saturated sodium bicarbonate-chloroform mixed solution (40 ml–100 ml). After extracting with chloroform, the resulting organic layer was washed with an aqueous saturated sodium chloride solution, dried on magnesium sulphate, and concentrated under vacuum. 2.91 g (15 mmol) of 4-benzyloxybutyric acid, 0.1 g of DMAP and dry acetonitrile (50 ml) were added immediately to dissolve the resulting residue. The admixture was stirred while cooled in an ice bath, a dry acetonitrile solution (10 ml) containing 3.1 g (15 mmol) of DCC was added, and the reaction was carried out for 16 hours. After drying under vacuum, the resulting concentrated residue was dissolved in 150 ml of chloroform and washed consecutively with 5% citric acid (30 ml×2), an aqueous saturated sodium bicarbonate solution (30 ml) and an aqueous saturated sodium chloride solution (30 ml×2). After drying on magnesium sulphate and concentrating under vacuum, the resulting residue was purified on silica gel column chromatography (180 g, hexane:chloroform:ethyl acetate=1:1:1) to obtain 6.065 g of the title compound as a white powder.

Yield: 83.9%, mp=100–105° C. $[\alpha]_D$=−20.7 (C=1.03, 24° C., methanol) NMR (500 MHz, in $CDCl_3$): $\delta_{TMS}$=1.85–2.48 (16H, m, β-$CH_2$ on Glu×2, γ-$CH_2$ on Glu×2, and BnO—$CH_2$—$\underline{CH}_2$—$\underline{CH}_2$—CO), 3.49 (2H, t, J=6 Hz, BnO—$CH_2$), 4.47 (1H, d, J=12 Hz, $PhCH_2O×1/2$), 4.49 (1H, d, J=12 Hz, $PhCH_2O×1/2$), 4.54–4.64 (2H, m, α-CH on Glu×2), 5.07 (1H, d, J=12 Hz, $PhCH_2OCO×1/2$), 5.08 (1H, d, J=12 Hz, $PhCH_2OCO×1/2$), 5.12 (1H, d, J=12 Hz, $PhCH_2OCO×1/2$), 5.15 (2H, s, $PhCH_2OCO×1/2$), 5.16 (1H, d, J=12 Hz, $PhCH_2OCO$), 6.49 (1H, d, J=7.5 Hz, NH), 6.59 (1H, d, J=7.5 Hz, NH), 7.20–7.40 (20H, m, $C_6H_5×4$), 10.0–10.8 (1H, br, $CO_2H$); IR (nujol): $vcm^{-1}$=3300(NH), 1740(COOBn), 1725 (COOBn), 1650(CONH), 1645(CONH); FAB-MS:$m^+/z$= 723($M+H^+$)

Example 1

Synthesis of N-benzyloxycarbonyl-L-glutamic acid α,γ-di-2—(2',3',4',6'-tetraacetyl-β-D-galactosyl-1') ethoxyethoxyethylamide To 0.506 g ($1.80×10^{-3}$ mol) of N-benzyloxycarbonyl-L-glutamic acid were added 0.539 g (1.3 equivalent, molar ratio=2.6) of N-hydroxysuccinimide and 15 ml of acetonitrile, and the resulting solution was stirred while cooled on ice. To this solution, 0.817 g (1.1 equivalent, molar ratio=2.2) of N,N-dicyclohexyl-carbodiimide was added, and the resulting reaction mixture was stirred at 14° C. for 14 hours.

Separately, to 2.388 g (1.0 equivalent, mol ratio 2.0) of 1-(2'-azidoethoxyethoxyethyl)-2,3,4,6-tetra-O-acetyl-β-D-galactopyranose were added 10 ml of acetonitrile, and the resulting solution was cooled on ice. To this solution, 403 μl [1.0 equivalent to 1—(2'-azidoethoxyethoxyethyl)-2,3,4,6-tetra-O-acetyl-β-D-galactopyranose] of N-methylmorpholine were added, the resulting solution was added to the abovementioned reaction mixture and the admixture was stirred at 4° C. for 18 hours. The precipitate was removed by filtration and the solvents were removed by distillation under vacuum. The residue thus obtained was dissolved in ethyl acetate and washed with water/an aqueous saturated sodium chloride solution (1/1), dried on magnesium sulphate, and the solvents were removed by reduced-pressure distillation. The residue was purified by chromatography on silica gel eluting with benzene:acetone=2:3 to obtain 1.366 g of the title compound as an amorphous colorless solid.

Yield: 63.0%. $^1$H-NMR (δ, $CDCl_3$): 1.99 (s, 6H, acetyl), 2.04–2.07 (m, 2H, Gluβ), 2.05 (s, 6H, acetyl), 2.05 (s, 3H, acetyl), 2.06 (s, 3H, acetyl), 2.15 (s, 6H, acetyl), 2.25–2.30 (m, 1H, Gluγ), 2.33–2.39 (m, 1H, Gluγ), 3.40–3.75 (m, 22H, ethyleneglycol moiety), 3.90–3.98 (m, 4H, GalClβ-OC$\underline{H}_2$$CH_2$O— and Gal C5-H), 4.10–4.14 (m, 2H, Gal C6-Ha), 4.16–4.22 (dd, 3H, Gal C6-Hb and Gluα), 4.54 (d, 1H, J1.2=7.8 Hz, Gal Cl-H), 4.55 (d, 1H, J1.2=7.8 Hz, GalCl-H), 5.01–5.04 (m, 2H, Gal C3-H), 5.09 (s, 2H, PhC$\underline{H}_2$O—), 5.18–5.22 (m, 2H, Gal C2-H), 5.39 (br d, 2H, Gal C4-H), 6.06 (d, 1H, J=6.8 Hz, ZN$\underline{H}$—), 6.64 (br s, 1H, —CON$\underline{H}$—), 7.16 (br s, 1H, —CON$\underline{H}$—), 7.29–7.38 (m, 5H, Ph(Z)); IR (KBr tab): 1751 $cm^{-1}$(C=O); $[\alpha]_D^{24}$=−8.6 (c=0.97, $CHCl_3$)

Example 2

Synthesis of N-t-butoxycarbonyl-γ-L-glutamyl-L-glutamic acid α',α,γ-tri-2-(2',3',4',6'-tetraacetyl-β-D-galactosyl-1') ethoxyethoxyethylamide To 1.061 g ($3.59×10^{-3}$ mol) of N-t-butoxycarbonyl-L-glutamyl-L-glutamic acid (12) were added 1.486 g (1.2 equivalent, molar ratio=3.6) of N-hydroxysuccinimide and 50 ml of acetonitrile, and the resulting solution was stirred while cooled on ice. To this solution, 2.442 g (1.1 equivalent, molar ratio=3.3) of N,N-dicyclohexylcarbodiimide were added, and the resulting reaction mixture was stirred at 4° C. for 27 hours.

Separately, to 6.962 g (1.03 equivalent, mol ratio 3.09) of 1—(2'-azidoethoxyethoxyethyl)-2,3,4,6-tetra-O-acetyl-β-D-galactopyranose were added 10 ml of acetonitrile, and the resulting solution was cooled on ice. To this solution, 1.17 ml [1.0 equivalent to 1-(2'-azidoethoxyethoxyethyl)-2,3,4, 6-tetra-O-acetyl-β-D-galactopyranose] of N-methylmorpholine were added, the resulting solution was added to the abovementioned reaction mixture and the admixture was stirred at 4° C. for 18 hours. The precipitate was removed by filtration and the solvents were removed by distillation under vacuum. The residue thus obtained was dissolved in ethyl acetate and washed with water/an aqueous saturated sodium chloride solution (1/1), dried on magnesium sulphate, and the solvents were removed by reduced-pressure distillation. The residue was purified by chromatography on silica gel eluting with chloroform-methanol= 20:1 to obtain 4.700 g of the title compound as an amorphous colorless solid.

Yield: 77.4%. $^1$H-NMR(δ, $CDCl_3$): 1.42 (s, 9H, t-Bu), 1.94–2.20 (m, 4H, Gluβ), 1.99 (s, 9H, acetyl), 2.05–2.06 (m, 18H, acetyl), 2.16 (s, 9H, acetyl), 2.25–2.40 (m, 4H, Gluγ), 3.32–3.76 (m, 33H, ethyleneglycol moiety), 3.91–4.00 (m, 6H, GalClβ-OC$\underline{H}_2$$CH_2$O— and Gal C5-H), 4.10$^{-4.15}$ (m, 4H, Gal C6-Ha and Boc-Gluα), 4.16–4.20 (dd, 3H, Gal C6-Hb), 4.38(br dd, 1H, Glu (Gluα)), 4.55–4.57 (m, 3H, Gal Cl-H), 5.02–5.05 (m, 3H, Gal C3-H), 5.17–5.22 (m, 3H, Gal C2-H), 5.39 (br d, 3H, Gal C4-H), 5.47 (d, 1H, BocN$\underline{H}$—), 6.93(br s, 1H, —CON$\underline{H}$—), 7.18–7.26 (m, 2H, —CON$\underline{H}$—), 7.68 (br s, 1H, —CON$\underline{H}$—)

Example 3

Synthesis of N-t-butoxycarbonyl-γ-L-glutamyl-L-glutamic acid α',α,γ-tri-2-(2',3',4',6'-tetraacetyl-β-D-glucosyl-1') ethoxyethoxyethylamide The title compound was obtained as an amorphous pale brown solid in the same manner as described in Example 2, except that 1-(2'-azidoethoxyethoxyethyl)-2,3,4,6-tetra-O-acetyl-β-D-glucopyranose was used instead of 1-(2'-azidoethoxyethoxyethyl)-2,3,4,6-tetra-O-acetyl-β-D-galactopyranose.

Yield: 67.0%. $^1$H-NMR (δ, $CDCl_3$):
1.42 (s, 9H, t-Bu), 1.92–2.16 (m, 4H, Gluβ), 2.01 (s, 9H, acetyl), 2.03 (s, 9H, acetyl), 2.05 (s, 6H, acetyl), 2.05 (s, 3H, acetyl), 2.09 (s, 9H, acetyl), 2.24–2.44 (m, 4H, Gluγ), 3.32–3.76 (m, 33H, ethyleneglycolmoiety), 3.92–3.98 (m, 3H, Glc Clβ-OC$\underline{H}_2$$CH_2$O—), 4.11 (br q, 1H, Boc-Gluα), 4.15 (dd, 1H, J5,6a=2.0 Hz, J6a, 6b=12.2 Hz, GlcC6-Ha), 4.27 (dd, 1H, J5,6a=4.8 Hz, J6a, 6b=12.2 Hz, Glc C6-Hb), 4.38 (br q, Glu(Gluα)), 4.59–4.60 (m, 3H, Glc Cl-H), 4.99 (br t, 3H, Glc C2-H), 5.09 (br t, 3H, Glc C4-H), 5.21 (br t, 3H, Glc C3-H), 5.45 (br d, 1H, BocNH—), 6.87 (br s, 1H, —CONH—), 7.19 (br s, 2H, —CONH— and Gluγ—CON H), 7.06 (br s, 1H, —CONH—) IR(KBr tab): 1757 cm$^{-1}$ (C=O)

Example 4

Synthesis of N-(10-hydroxydecanoyl)-L-glutamyl-L-glutamic acid α',α,γ-tri-2—(2',3',4',6'-tetraacetyl-β-D-galactosyl-1)hexylamide 2.31 g (4.8 mmol) of 1-(6'-azidohexyl)-2,3,4,6-tetra-O-acetyl-β-D-galactopyranose were dissolved in 50 ml of ethanol, and 750 mg of methanesulfonic acid and 2 g of Lindlar catalyst were added. The admixture was stirred under a hydrogen gas flow under pressure (50 psi) for 2 hours. After adding another 1 g of Lindlar catalyst, the admixture was again stirred under a hydrogen gas flow under pressure (50 psi) for 1 hour. The catalyst was removed by filtration, the filtrate was concentrated under vacuum, and the resulting residue was dissolved in 50 ml of dry acetonitrile to obtain an amine solution.

1.1 g (1.5 mmol) of the compound of Synthesis Example 2 were dissolved in a dioxane-water mixture (30 ml–10 ml), and 300 mg of 10% palladium-carbon catalyst were added. The admixture was stirred under a hydrogen gas flow under normal pressure for 20 hours. The catalyst was removed by filtration, the filtrate was concentrated under vacuum, and the resulting residue was dissolved in a dry acetonitrile-DMF mixture (20 ml–5 ml). 1.15 g (10 mmol) of N-hydroxysuccinimide were added, and the admixture was stirred while cooled in an ice-ethanol bath. 1.03 g of DCC were added, and the reaction was carried out at 0–5° C. for 4 hours. The precipitate was removed by filtration and washed with a small amount of acetonitrile to obtain an active ester solution.

The amine solution (6 mmol) and the active ester solution (1.5 mmol) were mixed while cooled on an ice bath, 10 mmol of diisopropylethylamine was added, and the reaction was carried out at 4° C. overnight. After concentration under vacuum, the resulting residue was dissolved in 150 ml of ethyl acetate, and washed consecutively with 5% citric acid (15 ml×4), an aqueous saturated sodium bicarbonate solution (15 ml×6) and an aqueous saturated sodium chloride solution (15 ml×2). After drying on magnesium sulphate, the residue was concentrated under vacuum and purified by chromatography on silica gel (150 g, eluting with chloroform:ethanol=30:1) to obtain 744 mg of the title compound as an amorphous white powder.

Yield: 28.6%. [α]$_D$=−11.3 (C=1.00, 26° C., methanol) NMR (500 MHz, in CDCl$_3$): δ$^{TMS}$=1.24–1.42 (22H, brm, —(CH$_2$)$_5$— on —(CH$_2$)$_9$— and —(CH$_2$)$_2$— on —(CH$_2$)$_6$—×3), 1.42–1.68 (16H, brm, —(CH$_2$)—×8), 1.8–2.45, 2.45–2.57,3.01 (46H, m, CH$_2$CO on decanoyl, CH$_3$CO×12, β-CH$_2$ on Glu×2, and γ-CH$_2$ on Glu×2), 3.1–3.25 (6H, m, NCH$_2$×3), 3.42–3.53 (3H, m, O-CH$_2$×½× 3), 3.64 (2H, m, changed with D20, HOCH$_2$), 3.83–3.95 (6H, m, 5-CH on Gal×3 and O—CH$_2$×½×3), 4.08–4.24 (6H, m, 6'-CH$_2$ on Gal×3), 4.38 (1H, m, α-CH on Glu), 4.46 (3H, d, J=8.5 Hz, 1'-CH on Gal×3), 4.64 (1H, m, α-CH on Glu), 5.00–5.06 (3H, m, 3'-CH on Gal×3), 5.19 (3H, m, 2'-CH on Gal×3), 5.39 (3H, m, 4'-CH on Gal×3), 6.25 (1H, t, J=6 Hz, NH—CH$_2$), 6.36 (1H, d, J=8 Hz, NH—CH), 6.63 (1H, t, J=6 Hz, NH—CH$_2$), 6.72 (1H, d, J=7 Hz, NH—CH), 7.06 (1H, t, J=6 Hz, NH—CH$_2$), 7.21 (1H, m, disappeared with D$_2$O, OH); IR(nujol): vcm$^{-1}$=3290(OH and CONH), 1750 (CH$_3$CO); FAB-MS: m$^+$/z=1734(M+H$^+$)

Example 5

Synthesis of N-(10-hydroxydecanoyl)-L-glutamyl-L-glutamic acid α',α,γ-tri-2-(2',3',4',6'-tetraacetyl-β-D-galactosyl-1)ethylamide 2.50 g (6 mmol) of 1-(2'-azidoethyl)-2,3,4,6-tetra-O-acetyl-β-D-galactopyranose were dissolved in 40 ml of ethanol, and 750 mg of methanesulfonic acid and 2 g of Lindlar catalyst were added. The admixture was stirred under a hydrogen gas flow under pressure (50 psi) for 2 hours. After adding another 1 g of Lindlar catalyst, the admixture was again stirred under a hydrogen gas atmosphere under pressure (50 psi) for 1 hour. The catalyst was removed by filtration, the filtrate was concentrated under vacuum, and the resulting residue was dissolved in 50 ml of dry acetonitrile to obtain an amine solution.

1.1 g (1.5 mmol) of the compound of Synthesis Example 2 were dissolved in a dioxane-water mixture (30 ml–10 ml), and 300 mg of 10% palladium-carbon catalyst were added. The admixture was stirred under a hydrogen gas atmosphere under normal pressure for 20 hours. The catalyst was removed by filtration, the filtrate was concentrated under vacuum, and the resulting residue was dissolved in a dry acetonitrile-DMF mixture (20 ml–5 ml). 1.15 g (10 mmol) of N-hydroxysuccinimide were added, and the admixture was stirred while cooled in an ice-ethanol bath. 1.03 g of DCC were added, and the reaction was carried out at 0–5° C. for 4 hours. The precipitate was removed by filtration and washed with a small amount of acetonitrile to obtain an active ester solution.

The amine solution (6 mmol) and the active ester solution (1.5 mmol) were mixed while cooled on an ice bath, 10 mmol of diisopropylethylamine was added, and the reaction was carried out at 4° C. overnight. After concentration under vacuum, the resulting residue was dissolved in 150 ml of ethyl acetate, and washed consecutively with 5% citric acid (15 ml×4), an aqueous saturated sodium bicarbonate solution (15 ml×6) and an aqueous saturated sodium chloride solution (15 ml×2). After drying on magnesium sulphate, the residue was concentrated under vacuum and purified by chromatography on silica gel (150 g, eluting with chloroform:ethanol=30:1→20:1) to obtain 1.33 g of the title compound as an amorphous white powder.

Yield: 56.6%. [α]$_D$=−8.9 (C=1.04, 24° C., methanol) NMR (500 MHz, in CDCl$_3$): δ$^{TMS}$=1.25–1.4 (10H brm, —(CH$_2$)$_5$—), 1.52–1.64 (4H, m, —(CH$_2$)$_2$—), 1.75 (1H, t, J=5 Hz, disappeared with D$_2$O, OH), 1.9–2.25 (42H, CH$_2$CO on decanoyl, CH$_3$CO×12 and β-CH$_2$ on Glu×2), 2.30–2.42 (4H, m, γ-CH$_2$ on Glu×2),3.36–3.52 (6H, brm, NCH$_2$×3), 3.60–3.74 (5H, m, changed with D$_2$O, HOCH$_2$ and O—CH$_2$×½×3), 3.84–3.98 (6H, m, 5'-CH on Gal×3 and O—CH$_2$×½×3), 4.08–4.22 (6H, m, 6'-CH$_2$ on Gal×3), 4.40–4.58 (5H, m, α-CH on Glu×2 and 1'-CH on Gal×3), 5.00–5.07 (3H, m, 3'-CH on Gal×3), 5.12–5.20 (3H, m, 2'-CH on Gal×3), 5.36–5.44 (3H, m, 4'-CH on Gal×3), 6.61 (1H, d, J=7.5 Hz, NH—CH), 6.93 (1H, t, J=6 Hz, NH—CH$_2$), 6.96 (1H, t, J=6 Hz, NH—CH$_2$), 7.15 (1H, d, J=7.5 Hz, NH—CH), 7.68 (1H, t, J=6 Hz, NH—CH); IR(nujol): vcm$^{-1}$=3280(OH of CONH), 1750(CH$_3$CO), 1635(CONH); FAB-MS:m$^+$/z=1566(M+H$^+$)

Example 6

Synthesis of N-(4-hydroxybutyroyl)-L-glutamyl-L-glutamic acid α',α,γ-tri-2-(2',3',4',6'-tetraacetyl-β-D-galactosyl-1) ethylamide 1.88 g (4.5 mmol) of 1-(2'-azidoethyl)-2,3,4,6-tetra-O-acetyl-β-D-galactopyranose were dissolved in 40 ml of ethanol, and 580 mg of methanesulfonic acid and 2 g of Lindlar catalyst were added. The admixture was stirred under a hydrogen gas flow under pressure (50 psi) for 2 hours. After adding another 1 g of Lindlar catalyst, the admixture was again stirred under a hydrogen gas atmosphere under pressure (50 psi) for 1 hour. The catalyst was removed by filtration, the filtrate was concentrated under vacuum, and the resulting residue was dissolved in 50 ml of dry acetonitrile to obtain an amine solution.

1.45 g (2 mmol) of the compound of Synthesis Example 3 were dissolved in a dioxane-water mixture (25 ml–10 ml), and 400 mg of 10% palladium-carbon catalyst were added. The admixture was stirred under a hydrogen gas flow under normal pressure for 18 hours. The catalyst was removed by filtration, the filtrate was concentrated under vacuum, and the resulting residue was dissolved in a dry acetonitrile-DMF mixture (30 ml–10 ml). 1.73 g (15 mmol) of N-hydroxysuccinimide were added, and the admixture was stirred while cooled in an ice-ethanol bath. 1.49 g of DCC were added, and the reaction was carried out for 5 hours. The precipitate was removed by filtration and washed with a small amount of acetonitrile to obtain an active ester solution. A half portion of the solution was used for the next reaction.

The amine solution (4.5 mmol) and the active ester solution (1 mmol) were mixed while cooled on an ice bath, 2 ml of diisopropylethylamine was added, and the reaction was carried out at 4° C. overnight. After concentration under vacuum, the resulting residue was dissolved in 80 ml of ethyl acetate, and washed consecutively with 5% citric acid (10 ml), an aqueous saturated sodium chloride solution (5 ml), an aqueous saturated sodium bicarbonate solution (10 ml×2) and an aqueous saturated sodium chloride solution (10 ml×2). After drying on magnesium sulphate, the residue was concentrated under vacuum and purified by chromatography on silica gel (100 g, eluting with chloroform:ethanol= 15:1) to obtain 622 mg of the title compound as an amorphous white powder.

Yield: 42.3%. $[\alpha]_D$=−11.9 (C=1.025, 26° C., methanol) NMR (500 MHz, in CDCl$_3$): $\delta^{TMS}$=1.89 (2H, quintet, J=6.5 Hz, CH$_2$—CH$_2$—OH), 1.93–2.22 (40H, m, CH$_3$CO×12 and β-CH$_2$ on Glu×2), 2.30–2.43 (6H, m, γ-CH$_2$ on Glu×2 and CH$_2$—CH$_2$—CH$_2$—OH), 2.99 (1H, brm, disappeared with D$_2$O, OH), 3.36–3.55 (6H, m, NHC$_2$×3), 3.65–3.74 (5H, m, O—CH$_2$×½×3 and CH$_2$OH), 3.85–3.99 (6H, m, 5'-CH on Gal×3 and O—CH$_2$×½×3), 4.08–4.22 (6H, m, 6'-CH$_2$ on Gal×3), 4.37–4.50 (2H, m, α-CH on Glu×2), 4.48–4.56 (3H, m, 1'-CH on Gal×3), 5.01–5.06 (3H, m, 3'-CH on Gal×3), 5.12–5.18 (3H, m, 2'-CH on Gal×3), 5.40 (3H, d, J=3.5 Hz, 4'-CH on Gal×3), 6.80 (1H, t, J=5.5 Hz, NH—CH$_2$), 6.88 (1H, d, J=7.5 Hz, NH—CH), 6.93 (1H, t, J=5.5 Hz, NH—CH$_2$), 7.13 (1H, d, J=7 Hz, NH—CH), 7.54 (1H, t, J=7.5 Hz, NH—CH) IR(nujol): νcm$^{-1}$=3280(OH of CONH), 1750(CH$_3$CO), 1635(CONH); FAB-MS:m$^+$/z= 1482(M+H$^+$)

Example 7

Synthesis of N-(4-hydroxybutynoyl)-L-glutamyl-L-glutamic acid α',{α,γ-tri-2-(2',3',4',6'-tetraacetyl-β-D-galactosyl-1)ethoxy}ethoxyethylamide 2.27 g (4.5 mmol) of 1-(2'-azidoethoxyethoxyethyl)-2,3, 4,6-tetra-O-acetyl-β-D-galactopyranose were dissolved in 40 ml of ethanol, and 580 mg of methanesulfonic acid and 2 g of Lindlar catalyst were added. The admixture was stirred under a hydrogen gas atmosphere under pressure (50 psi) for 2 hours. After adding another 1 g of Lindlar catalyst, the admixture was again stirred under a hydrogen gas atmosphere under pressure (50 psi) for 1 hour. The catalyst was removed by filtration, the filtrate was concentrated under vacuum, and the resulting residue was dissolved in 50 ml of dry acetonitrile to obtain an amine solution.

1.45 g (2 mmol) of the compound of Synthesis Example 3 were dissolved in a dioxane-water mixture (25 ml–10 ml), and 400 mg of 10% palladium-carbon catalyst were added. The admixture was stirred under a hydrogen gas atmosphere under normal pressure for 18 hours. The catalyst was removed by filtration, the filtrate was concentrated under vacuum, and the resulting residue was dissolved in a dry acetonitrile-DMF mixture (30 ml–10 ml). 1.73 g (15 mmol) of N-hydroxysuccinimide were added, and the admixture was stirred while cooled in an ice-ethanol bath. 1.49 g of DCC were added, and the reaction was carried out for 5 hours. The precipitate was removed by filtration and washed with a small amount of acetonitrile to obtain an active ester solution. A half portion of the solution was used for the next reaction.

The amine solution (4.5 mmol) and the active ester solution (1 mmol) were mixed while cooled on an ice bath, 2 ml of diisopropylethylamine was added, and the reaction was carried out at 4° C. overnight. After concentration under vacuum, the resulting residue was dissolved in 80 ml of ethyl acetate, and washed consecutively with 5% citric acid (10 ml), an aqueous saturated sodium chloride solution (5 ml), an aqueous saturated sodium bicarbonate solution (10 ml×2) and an aqueous saturated sodium chloride solution (10 ml×2). After drying on magnesium sulphate, the residue was concentrated under vacuum and purified by chromatography on silica gel (100 g, eluting with chloroform:ethanol= 10:1) to obtain 697 mg of the title compound as a colorless caramel-like solid.

Yield: 43.5%. $[\alpha]_D$=−11.0 (C=1.00, 26° C., metanol) NMR (500 MHz, in CDCl$_3$): $\delta^{TMS}$=1.82–1.94 (2H, m, CH$_2$—CH$_2$—OH), 1.92–2.20 (40H, m, CH$_3$CO×12 and β-CH$_2$ on Glu×2), 2.27–2.44 (6H, m, γ-CH$_2$ on Glu×2 and β-CH$_2$ on Glu×2), CH$_2$—CH$_2$—CH$_2$—OH), 3.21 (1H, t, J=5 Hz, disappeared with D$_2$O, OH), 3.33–3.76 (35H, m, NCH$_2$×3, OCH$_2$×12, O—CH$_2$-Gal×½×3 and CH$_2$OH), 3.92–4.00 (6H, m, 5'-CH on Gal×3 and O—CH$_2$×½×3), 4.08–4.22 (6H, m, 6'-CH$_2$ on Gal×3), 4.35–4.46 (2H, m, α-CH on Glu×2), 4.54–4.60 (3H, m, 1'-CH on Gal×3), 5.02–5.08 (3H, m, 3'-CH on Gal×3), 5.16–5.22 (3H, m, 2'-CH on Gal×3), 5.39 (3H, d, J=3.5 Hz, 4'-CH on Gal×3), 6.93 (1H, d, J=7.5 Hz, NH—CH), 6.99 (1H, t, J=5.5 Hz, NH—CH$_2$), 7.08 (1H, t, J=5.5 Hz, NH—CH$_2$), 7.22 (1H, d, J=7.5 Hz, NH—CH), 7.68 (1H, t, J=5.5 Hz, NH—CH); IR(nujol): νcm$^{-1}$=3280(OH of CONH), 1750 (CH$_3$CO), 1635(CONH); FAB-MS:m$^+$/z= 1746(M+H$^+$)

Example 8

Synthesis of N-(10-hydroxydecanoyl)-L-glutamyl-L-glutamic acid α',α,γ-tri-2-(2',3',4',6'-tetraacetyl-β-D-galactosamine-1)octylamide (1) Synthesis of 1-(8-azidooctyl)-2,3,4,6-tetraacetyl-β-D-galactosamine 1.35 g of anhydrous ferrous chloride and anhydrous magnesium sulphate were mixed in 40 ml of methylene chloride, and 1.71 g (10 mmol) of 8-azido-octanol and 2.0 g (5.14 mmol) of 2-deoxy-2-acetamide-β-D-galactopyranose-tetra-O-acetate were added to this mixture at room temperature with stirring. After reaction by stirring at room temperature for 6 hours, the admixture was filtered, and the filtrate was washed consecutively with an aqueous saturated sodium bicarbonate solution and an aqueous saturated sodium chloride solution. After drying on magnesium sulphate and concentrating under vacuum, the resulting residue was purified by chromatography on silica gel to obtain 1.77 g of the title compound as a colorless caramel-like solid.

Yield: 68.8% $[\alpha]_D$=−15.9 (C=1.12, 26° C., methanol) NMR (500 MHz, in CDCl$_3$): $\delta^{TMS}$=1.25–1.40 (8H, brm, —(CH$_2$)$_4$—), 1.55–1.64 (4H, m, —CH$_2$—×2), 1.96 (3H, s, CH$_3$ on Ac), 2.01 (3H, s, CH$_3$ on Ac), 2.05 (3H, s, CH$_3$ on Ac), 2.14 (3H, s, CH$_3$ on Ac), 3.26 (2H, t, J=7 Hz, N$_3$-CH$_2$), 3.48 (1H, ddd, J=9.5, 7, and 7 Hz, OCH$_2$×½), 3.85–3.95 (3H, m, OCH$_2$×1/2, 2'-CH on Gal NAc, 5'-CH on GalNAc), 4.13 (1H, dd, J=11 and 7 Hz, 6'-CH$_2$ on GalNAc×1/2), 4.17 (1H, dd, J=11 and 7 Hz, 6'-CH$_2$ on GalNAc×1/2), 4.72 (1H, d, J=8.5, 1'-CH on GalNAc), 5.28–5.40 (3H, m, 3'-CH on GalNAc, 4'-CH on GalNAc); IR(nujol): vcm$^{-1}$=3290(NH), 2100(N$_3$), 1750(CH$_3$CO); FAB-MS:m/z=501(M+H$^+$)

(2) Synthesis of N-(10-hydroxydecanoyl)-L-glutamyl-L-glutamic acid α',α,γ-tri-2-(2',3',4',6'-tetraacetyl-β-D-galactosamine-1)octylamide 1.75 g (3.5 mmol) of the compound obtained in (1) above were dissolved in 40 ml of ethanol, and 650 mg of methanesulfonic acid and 2 g of Lindlar catalyst were added. The admixture was stirred under a hydrogen gas atmosphere under pressure (50 psi) for 2 hours. After adding another 1 g of Lindlar catalyst, the admixture was again stirred under a hydrogen gas atmosphere under pressure (50 psi) for 1 hour. The catalyst was removed by filtration, the filtrate was concentrated under vacuum, and the resulting residue was dissolved in 50 ml of dry acetonitrile to obtain an amine solution.

717 mg (1 mmol) of the compound of Synthesis Example 2 were dissolved in a dioxane-water mixture (20 ml–10 ml), and 300 mg of 10% palladium-carbon catalyst were added. The admixture was stirred under a hydrogen gas atmosphere under normal pressure for 20 hours. The catalyst was removed by filtration, the filtrate was concentrated under vacuum, and the resulting residue was dissolved in a dry acetonitrile-DMF mixture (20 ml–7 ml). 1.15 g (10 mmol) of N-hydroxysuccinimide were added, and the admixture was stirred while cooled in an ice-ethanol bath. 825 mg of DCC was added, and the reaction was carried out at 0–5° C. for 18 hours. The precipitate was removed by filtration and washed with a small amount of acetonitrile to obtain an active ester solution.

The amine solution (3.5 mmol) and the active ester solution (1 mmol) were mixed while cooled on an ice bath, 10 mmol of diisopropylethylamine was added, and the reaction was carried out at 4° C. overnight. After concentration under vacuum, the resulting residue was dissolved in 150 ml of ethyl acetate, and washed consecutively with 5% citric acid (15 ml×4), an aqueous saturated sodium bicarbonate solution (15 ml×6) and an aqueous saturated sodium chloride solution (15 ml×2). After drying on magnesium sulphate, the residue was concentrated under vacuum and purified by chromatography on silica gel (150 g, eluting with chloroform:ethanol=30:1) to obtain 547 mg of the title compound as an amorphous white powder.

Yield: 30.1%. [α]$_D$=−17.6(C=0.99, 27° C., methanol); NMR(500 MHz, in CDCl$_3$): δ$^{TMS}$=1.20–1.38 (34H, brm, —(CH$_2$)$_5$— on —(CH$_2$)$_9$— and —(CH$_2$)$_4$— on —(CH$_2$) 8—×3), 1.40–1.66 (16H, brm, —(CH$_2$)—×8), 1.80–2.45 (46H, m, CH$_2$CO on decanoyl, CH$_3$CO×12, β-CH$_2$ on Glu×2, and γ-CH$_2$ on Glu×2), 3.10–3.35 (6H, m, NCH$_2$×3), 3.40–3.52 (3H, m, O—CH$_2$×½×3), 3.60–3.69 (2H, m, changed with D$_2$O, HOC<u>H</u>$_2$), 3.85–4.25 (15H, m, 2'-CH on GalNAc×3, 5'-CH on GalNAc×3, 6'-CH$_2$ on GalNAc×3, and O—CH$_2$×½×3), 4.44–4.55 (2H, brm, NH×2), 4.60–4.73 (3H, m, 1'-CH on GalNAc×3), 5.25–5.42 (6H, m, 3'-CH on GalNAc×3, 4'-CH on GalNAc×3), 6.26–6.48 (2H, m, NH×2), 6.83 (1H, d, J=7 Hz, NH), 6.97 (1H, t, J=5 Hz, OH), 7.32–7.45 (2H, m, NH×2), 7.89–7.94 (1H, m, NH); IR(nujol): vcm$^{-1}$=3280(OH and CONH), 1750(CH$_3$CO); FAB-MS:m$^+$/z=1815(M+H$^+$)

Example 9

Synthesis of N-(4-hydroxybutyroyl)-L-glutamic acid α,γ-di-{2-(2',3',4',6'-tetraacetyl-β-D-galactosyl-1)ethoxy}ethoxyethylamide (1) Synthesis of N-(4-benzyloxybutyroyl)-L-glutamic acid α,γ-dibenzyl ester 7.97 g (16 mmol) of L-glutamic acid α,γ-dibenzyl ester p-toluenesulfonate were dissolved in 30 ml of dry acetonitrile, and 4 ml of diisopropylethylamine was added while cooled in an ice water bath to obtain an amine solution.

1.5 g of 4-benzyloxybutyric acid were dissolved in dry acetonitrile-DMF (30 ml–9 ml). 2.13 g of N-hydroxysuccinimide were added, and the admixture was stirred while cooled in an ice water bath. 1.91 g of DCC were added, and the reaction was carried out for 5 hours. The precipitate was removed by filtration and washed with a small amount of acetonitrile to obtain an active ester solution.

The amine solution and the active ester solution thus prepared were mixed while cooled in an ice bath, and the reaction was carried out at 0° C. for 2 hours. After concentration under vacuum, the resulting residue was dissolved in chloroform, and washed consecutively with a 5% aqueous citric acid solution, an aqueous saturated sodium bicarbonate solution, an aqueous saturated sodium hydrogen carbonate solution and an aqueous saturated sodium chloride solution. After drying on magnesium sulphate anhydrous, the residue was concentrated under vacuum and purified by chromatography on silica gel (200 g, eluting with methylene chloride:ethanol=50:1–20:1) to obtain 1.59 g of the title compound as an amorphous yellow powder.

Yield: 41%. [α]$_D^{24}$−16.4 (c0.88, MeOH); IR (CHCl$_3$): 1735cm$^{-1}$, 1674cm$^{-1}$, 1171cm$^{-1}$; $^1$H-NMR(CDCl$_3$)δ: 7.35–7.31 (15H, m, Ph-<u>H</u>×3), 6.31 (1H, brs, NH), 5.15 (2H, slike, C<u>H</u>$_2$Ph), 5.10,5.07 (each 1H, J=14.5 Hz, CH$_2$Ph), 4.67–4.63 (1H, m, Glu-α), 4.49,4.46 (each 1H, J=12.0 Hz, C<u>H</u>$_2$Ph), 3.50 (1H, tlike, Glu-γ), 2.44–2.16 (5H, m, etylene moiety), 1.99–1.89 (3H, m, etylene moiety, Glu-β)

(2) Synthesis of N-(4-hydroxybutyroyl)-L-glutamic acid α,γ-di-{(2—(2',3',4',6'-tetraacetyl-β-D-galactosyl-1)ethoxy}ethoxyethylamide 2.8 g (5.6 mmol) of 1-(2'-azidoethoxyethoxyethyl)-2,3,4,6-tetra-O-acetyl-β-D-galactopyranose were dissolved in 60 ml of ethanol, and 761 mg (8.4 mmol) of methanesulfonic acid and 3 g of Lindlar catalyst were added. The admixture was stirred under a hydrogen gas flow under pressure (50 psi) for 2 hours. After adding another 1.5 g of Lindlar catalyst, the admixture was again stirred under a hydrogen gas flow under pressure (50 psi) for 1 hour. The catalyst was removed by filtration, the filtrate was concentrated under vacuum, and the resulting residue was dissolved in 50 ml of dry acetonitrile to obtain an amine solution.

1.0 g (2.0 mmol) of the compound of (1) above was dissolved in a dioxane-water mixture (20 ml–7.5 ml), and 300 mg of 10% palladium-carbon catalyst were added. The admixture was stirred under a hydrogen gas flow under normal pressure for 12 hours. The catalyst was removed by filtration, the filtrate was concentrated under vacuum, and the resulting residue was dissolved in a dry acetonitrile-DMF mixture (25 ml–7.5 ml). 1.1 g (9.6 mmol) of N-hydroxysuccinimide were added, and the admixture was stirred while cooled in an ice-water bath. 1.0 g (4.8 mmol) of DCC was added, and the reaction was carried out for 4 hours. The precipitate was removed by filtration and washed with a small amount of acetonitrile to obtain an active ester solution.

The abovementioned amine solution (5.6 mmol) and the active ester solution (2.0 mmol) were mixed while cooled on an ice-water bath, 2.5 ml of diisopropylethylamine was added, and the reaction was carried out at 0° C. for 14 hours. After concentration under vacuum, the resulting residue was dissolved in chloroform, and washed consecutively with a 5% aqueous citric acid solution, an aqueous saturated sodium chloride solution, an aqueous saturated sodium bicarbonate solution and an aqueous saturated sodium chloride solution. After drying on anhydrous magnesium sulphate, the residue was concentrated under vacuum and purified by chromatography on silica gel (60 g, eluting with chloroform:ethanol=15:1) to obtain 707 mg of the title compound as an amorphous orange powder. $[\alpha]_D^{24}$ −10.7° (c1.22, MeOH) IR(CHCl$_3$): 1749 cm$^{-1}$, 1661 cm$^{-1}$, 1078 cm$^{-1}$; $^1$H-NMR(CDCl$_3$) δ: 7.43 (1H, t, J=5.6 Hz, N$\underline{H}$CO), 7.31 (1H, d, J=9.3 Hz, N$\underline{H}$CO), 6.62 (1H, t, J=5.4 Hz, N$\underline{H}$CO), 5.40 (2H, d, J=3.4 Hz, Gal-4×2), 5.22–5.18 (2H, m, Gal-2×2), 5.05–5.02 (2H, m, Gal-3×2), 4.57–4.55 (2H, m, Gal-1×2), 4.42–4.37 (1H, m, Glu-α), 4.21–4.11 (4H, m, Gal-6×2), 4.00–3.96 (2H, m, etyleneglycol moiety), 3.95–3.92 (2H, m, Gal-5×2), 3.76–3.35 (22H, m, ethylenglycol moiety), 3.24 (1H, brs, O$\underline{H}$), 2.43–2.27 (6H, m, Glu-g, ethylene moiety, Glu-b), 2.16, 2.06, 2.05, 1.99 (each s, 6H, acetyl), 1.97–1.82 (2H, m, etylene moiety)

Reference Example 1

Synthesis of N-(4-hydroxybutyroyl)-{2'-(2',3',4',6'-tetraacetyl-β-D-galactosyl-1)-ethoxy}ethoxyethylamide (1) Synthesis of N-(4-benzyloxybutyroyl)-{2'-(2',3',4',6'-tetraacetyl-β-D-galactosyl-1)ethoxy}ethoxyethylamide 1.0 g (2.0 mmol) of 1-(2'-azidoethoxyethoxyethyl)-2,3,4,6-tetra-O-acetyl-β-D-galactopyranose was dissolved in 20 ml of ethanol, and 285 mg of methanesulfonic acid and 1.0 g of Lindlar catalyst were added. The admixture was stirred under a hydrogen gas atmosphere under pressure (50 psi) for 2 hours. After adding another 0.5 g of Lindlar catalyst, the admixture was again stirred under a hydrogen gas atmosphere under pressure (50 psi) for 2 hour.

The catalyst was removed by filtration, the filtrate was concentrated under vacuum, and the resulting residue was dissolved in dry acetonitrile to obtain an amine solution.

256 mg (1.3 mmol) of 4-benzyloxybutyric acid were dissolved in a dry acetonitrile-DMF mixture (5 ml–1.5 ml). 365 mg (3.2 mmol) of N-hydroxysuccinimide were added, and the admixture was stirred while cooled in an ice-water bath. 326 mg (1.6 mmol) of DCC were added, and the reaction was carried out at 0° C. for 5 hours. The precipitate was removed by filtration and washed with a small amount of acetonitrile to obtain an active ester solution.

The amine solution (2.0 mmol) and the active ester solution (1.3 mmol) were mixed while cooled on an ice-water bath, 1 ml of diisopropylethylamine was added, and the reaction was carried out at 0° C. overnight. After concentration under vacuum, the resulting residue was dissolved in chloroform, and washed consecutively with a 5% aqueous citric acid solution, an aqueous saturated sodium bicarbonate solution and an aqueous saturated sodium chloride solution. After drying on anhydrous magnesium sulphate, the residue was concentrated under vacuum and purified by chromatography on silica gel (5.0 g, eluting with methylene chloride:methanol=20:1) to obtain 429 mg of the title compound as a pale yellow oil.

Yield: 30%. $[\alpha]_D^{23}$ −9.1° (c1.00, CHCl$_3$); IR(CHCl$_3$): 1749 cm$^{-1}$, 1664 cm$^{-1}$, 1078cm$^{-1}$; $^1$H-NMR(CDCl$_3$) δ:

7.36–7.27 (5H, m, Ph-$\underline{H}$), 6.12 (1H, brs, N$\underline{H}$), 5.39 (1H, dlike, Gal-4), 5.21 (1H, dd, J=7.9 Hz, J=10.5 Hz, Gal-2), 5.02 (1H, dd, J=2.7 Hz, J=10.5 Hz, Gal-3), 4.53 (1H, d, J=7.9 Hz, Gal-1), 4.50 (2H, slike, C$\underline{H}_2$Ph), 4.17 (1H, dd, J=11.5 Hz, J=6.6 Hz, Gal-6), 4.12 (1H, dd, J=11.5 Hz, J=6.6 Hz, Gal-6), 3.99–3.95 (1H, m), 3.89 (1H, tlike, Gal-5), 3.74–3.70 (1H, m), 3.65–3.51 (10H, m), 3.45–3.42 (2H, m, C$\underline{H}_2$CONH), 2.31 (2H, tlike, C$\underline{H}_2$NH), 2.14, 2.05, 2.05, 1.99 (each 3H, s, acetyl), 1.97–1.94 (2H, m, C$\underline{H}_2$OCH$_2$Ph)

(2) Synthesis of N-(4-hydroxybutynoyl)-{2'-(2',3',4,6'-tetraacetyl-β-D-galactosyl-1)ethoxy}ethoxyethylamide 200 mg (2.4 mmol) of the compound of (1) above were dissolved in 5 ml of ethyl acetate, and 10% palladiumcarbon was added. The admixture was stirred under a hydrogen gas atmosphere under normal pressure for 3 hours. The catalyst was removed by filtration, the filtrate was concentrated under vacuum, and the resulting residue was purified by chromatography on silica gel (2 g, methylene chloride:methanol=20:1) to obtain 117 mg of the title compound as a colorless oil.

Yield: 86% $[\alpha]_D^{24}$ −5.9° (c1.00, MeOH); IR(CHCl$_3$): 3450 cm$^{-1}$, 1749 cm$^{-1}$, 1651 cm$^{-1}$, 1078 cm$^{-1}$; $^1$H-NMR (CDCl$_3$)δ: 6.49 (1H, brs, N$\underline{H}$), 5.39 (1H, dlike, Gal-4), 5.20 (1H, dd, J=8.0 Hz, J=10.5 Hz, Gal-2), 5.03 (1H, dd, J=3.4 Hz, J=10.5 Hz, Gal-3), 4.55 (1H, d, J=8.0 Hz, Gal-1), 4.19 (1H, dd, J=6.5 Hz, J=11.2 Hz, Gal-6), 4.12 (1H, dd, J=6.8 Hz, J=11.2 Hz, Gal-6), 4.02–3.98 (1H, m, ethyleneglycol moiety), 3.92 (1H, tlike, Gal-5), 3.76–3.59 (9H, m, etyleneglycol moiety), 3.56 (2H, tlike, C$\underline{H}_2$NH), 3.48–3.44 (2H, m, C$\underline{H}_2$OH), 3.20–3.02 (1H, brs, OH), 2.39 (2H, tlike, C$\underline{H}_2$CONH), 2.16, 2.07, 2.05, 1.99 (each 3H, s, acetyl), 1.91–1.86 (2H, m, CH$_2$CH$_2$OH)

Example 10

Synthesis of Phosphoroamidite (1)

175 mg (0.1 mmol) of the compound of Example 4 were dissolved in 20 ml of dry methylene chloride, and 100 mg (0.33 mmol) of 2-cyanoethyl-N,N,N',N'-tetraisopropylphosphoroamidite were added while stirring on an ice-ethanol bath under a nitrogen gas flow. 0.3 ml of a 0.5 M tetrazole-acetonitrile solution was added dropwise at −5 to −10° C. After stirring at room temperature for 2.5 hours, 30 ml of a cooled 1 M aqueous triethyl ammonium hydrogencarbonate solution were added, and the admixture was further stirred for 10 minutes. The organic layer was isolated, washed consecutively with a 1 M aqueous triethyl ammonium hydrogencarbonate solution (10 ml) and an aqueous saturated sodium chloride solution, dried on magnesium sulphate, and concentrated under vacuum. The resulting residue was washed with hexane (30 ml×3) and dried under vacuum to obtain 226 mg of phosphoroamidite as an amorphous white powder.

Yield: quantitative. NMR(500 MHz, in CDCl$_3$): $δ^{TMS}$= 1.18–1.40 (34H, m, -CH$_3$ on iPrN×4, —(CH$_2$)$_5$— on —(CH$_2$)$_9$— and —(CH$_2$)$_2$— on —(CH$_2$)$_6$—×3), 1.44–1.66 (16H, m, —(CH$_2$)—×8), 1.85–2.57 (44H, m, CH$_3$CO×12 and β-CH$_2$ on Glu×2, γ-CH$_2$ on Glu×2 and CH$_2$CO on decanoyl), 2.65 (2H, t, J=6.5 Hz, CH$_2$CN), 3.10–3.36 (6H, m, NCH$_2$×3), 3.42–3.70 (9H, m, P-O-CH$_2$×2, NCH on iPr×2, and OCH$_2$-Gal=½×3), 3.75–3.94 (6H, m, 5'-CH on Gal×3,and OCH$_2$-Gal×½×3), 4.08–4.24 (6H, m, 6'-CH$_2$ on Gal×3), 4.38 (1H, m, α-CH on Glu), 4.46 (3H, d, J=8 Hz, Gal×3), 4.64 (1H, m, α-CH on Glu), 5.00–5.05 (3H, m, 3'-CH on Gal×3), 5.16–5.22 (3H, m, 2'-CH on Gal×3), 5.39 (3H, m, 4'-CH on Gal×3), 6.24 (1H, t, J=5 Hz, N$\underline{H}$—CH$_2$), 6.35 (1H, t, J=7 Hz, N$\underline{H}$—CH), 6.48 (1H, t, J=5 Hz, N$\underline{H}$—CH$_2$), 6.68 (1H, d, J=7 Hz, N$\underline{H}$—CH), 7.75 (1H, J=5 Hz, N$\underline{H}$—CH$_2$)

Example 11
Synthesis of Phosphoroamidite (2)

783 mg (0.5 mmol) of the compound of Example 5 were dissolved in 20 ml of dry methylene chloride, and 226 mg (0.75 mmol) of 2-cyanoethyl-N,N,N',N'-tetraisopropyl-phosphoroamidite were added while stirring on an ice-ethanol bath under a nitrogen gas flow. 1 ml of a 0.5 M tetrazole-acetonitrile solution was added dropwise at −5 to −10° C. After stirring at room temperature for 1 hour, 50 ml of a cooled 1 M aqueous triethyl ammonium hydrogencarbonate solution were added, and the admixture was further stirred for 10 minutes. The organic layer was isolated, washed consecutively with a 1 M aqueous triethyl ammonium hydrogencarbonate solution (10 ml) and an aqueous saturated sodium chloride solution, dried on magnesium sulphate, and concentrated under vacuum. The resulting residue was washed with hexane (30 ml×3) and dried under vacuum to obtain 833 mg of phosphoroamidite as an amorphous white powder.

Yield: 94.3%. NMR(500 MHz, in CDCl$_3$): $\delta^{TMS}$=1.17 (6H, d, J=6 Hz, —(CH$_3$)$_2$ on iPrN), 1.18 (6H, d, J=6 Hz, —(CH$_3$)$_2$ on iPrN), 1.20–1.38 (10H brm, —(CH$_2$)$_5$—), 1.55–1.66 (4H, m, —(CH$_2$)$_2$—), 1.90–2.18 (42H, m, CH$_3$CO×12 and β-CH$_2$ on Glu×2 and CH$_2$CO on decanoyl), 2.28–2.44 (4H, m, γ-CH$_2$ on Glu×2), 2.65 (2H, t, J=6.5 Hz, CH$_2$CN), 3.35–3.53 (6H, m, NCH$_2$× 3), 3.53–3.74 (7H, m, P—O—CH$_2$, NCH on iPr×2, and OCH$_2$-Gal×½×3), 3.75–3.98 (8H, m, 5'-CH on Gal×3, CH$_2$CH$_2$CN and OCH$_2$-Gal×½×3), 4.07–4.22 (6H, m, 6'-CH$_2$ on Gal×3), 4.40–4.52 (2H, m, α-CH on Glu×2), 4.50–4.55 (3H, m, 1'-CH on Gal×3), 5.00–5.06 (3H, m, 3'-CH on Gal×3), 5.13–5.19 (3H, m, 2'-CH on Gal×3), 5.35–5.45 (3H, m, 4'-CH on Gal×3), 6.56 (1H, d, J=7.5 Hz, NH—CH), 6.88 (1H, t, J=6 Hz, NH—CH$_2$), 6.95 (1H, t, J=5.5 Hz, NH—CH$_2$), 7.13 (1H, d, J=7.5 Hz, NH—CH), 7.72 (1H, d, J=5.5 Hz, NH—CH$_2$); IR(nujol): νcm$^{-1}$=3290(CONH), 1755(CH$_3$CO), 1635 (CONH)

Example 12
Synthesis of Phosphoroamidite (3)

641 mg (0.4 mmol) of the compound of Example 7 were dissolved in 20 ml of dry methylene chloride, and 181 mg (0.6 mmol) of 2-cyanoethyl-N,N,N',N'-tetraisopropyl-phosphoroamidite were added while stirring on an ice-ethanol bath under a nitrogen gas flow. 1 ml of a 0.5 M tetrazole-acetonitrile solution was added dropwise at −5 to −10° C. After stirring at room temperature for 3 hours, 40 ml of a cooled 1 M aqueous triethyl ammonium hydrogencarbonate solution were added, and the admixture was further stirred for 10 minutes. The organic layer was isolated, washed consecutively with a 1 M aqueous triethyl ammonium hydrogencarbonate solution (10 ml) and an aqueous saturated sodium chloride solution, dried on magnesium sulphate, and concentrated under vacuum. The resulting residue was washed with hexane (30 ml×3) and dried under vacuum to obtain 752 mg of phosphoroamidite as an amorphous white powder.

Yield: quantitative. NMR (500 MHz, in CDCl$_3$): $\delta^{TMS}$= 1.17 (6H, d, J=6.5 Hz, —(CH$_3$)$_2$ on iPrN), 1.18 (6H, d, J=6.5 Hz, —(CH$_3$)$_2$ on iPrN), 1.88–2.20 (42H, m, CH$_3$CO×12 and β-CH$_2$ on Glu×2 and CH$_2$—O—P), 2.26–2.43 (6H, m, γ-CH$_2$ on Glu×2 and CH$_2$CO on butyloyl), 2.66 (2H, t, J=6.5 Hz, CH$_2$CN), 3.30–3.92 (39H, m, NCH$_2$×3, OCH$_2$× 12, NCH on iPr×2, OCH$_2$ on butyloyl, CH$_2$CH$_2$CN, and OCH$_2$-Gal×½×3), 3.90–4.00 (6H, m, 5'-CH on Gal×3 and OCH$_2$-Gal×½×3), 4.09–4.24 (6H, m, 6'-CH$_2$ on Gal×3), 4.33–4.47 (2H, m, α-CH on Glu×2), 4.54–4.60 (3H, m, 1'-CH on Gal×3), 5.02–5.08 (3H, m, 3'-CH on Gal×3), 5.16–5.24 (3H, m, 2'-CH on Gal×3), 5.39 (3H, d, J=3.5 Hz, 4'-CH on Gal×3), 6.60 (1H, d, J=7.5 Hz, NH—CH), 7.02–7.07 (1H, m, NH—CH$_2$), 7.10–7.16 (1H, m, NH—CH$_2$), 7.23 (1H, d, J=7.5 Hz, NH—CH), 7.80–7.86 (1H, m, NH—CH)

Example 13
Synthesis of Phosphoroamidite (4)

181 mg (0.1 mmol) of the compound of Example 8 were dissolved in 20 ml of dry methylene chloride, and 100 mg (0.33 mmol) of 2-cyanoethyl-N,N,N',N'-tetraisopropyl-phosphoroamidite were added while stirring on an ice-ethanol bath under a nitrogen gas flow. 0.3 ml of a 0.5 M tetrazole-acetonitrile solution was added dropwise at −5 to −10° C. After stirring at room temperature for 2.5 hours, 30 ml of a cooled 1 M aqueous triethyl ammonium hydrogencarbonate solution were added, and the admixture was further stirred for 10 minutes. The organic layer was isolated, washed consecutively with a 1 M aqueous triethyl ammonium hydrogencarbonate solution (10 ml) and an aqueous saturated sodium chloride solution, dried on magnesium sulphate, and concentrated under vacuum. The resulting residue was washed with hexane (30 ml×3) and dried under vacuum to obtain 168 mg of phosphoroamidite as an amorphous white powder.

Yield: 85%. NMR (500 MHz, in CDCl$_3$): $\delta^{TMS}$=1.18–1.38 (46H, m, —CH$_3$ on iPrN×4, —(CH$_2$)$_5$— on —(CH$_2$)$_9$— and —(CH$_2$)$_4$— on —(CH$_2$)$_6$—×3), 1.44–1.70 (16H, m, —(CH$_2$)—×8), 1.85–2.45 (44H, m, CH$_3$CO×12 and β-CH$_2$ on Glu×2, γ-CH$_2$ on Glu×2 and CH$_2$CO on decanoyl), 2.65 (2H, t, J=6.5 Hz, CH$_2$CN), 3.10–3.36 (6H, m, NCH$_2$×3), 3.40–3.50 (7H, m, P—O—CH$_2$, NCH on iPr×2, and OCH$_2$-Gal×½×3), 3.76–4.24 (17H, m, 2'-CH on GalNAc×3, 5'-CH on GalNAc×3, 6'-CH$_2$ on GalNAc×3, O-CH$_2$—CH$_2$CN, and OCH$_2$-Gal×½×3), 4.40–4.60 (2H, m, α-CH on Glu×2), 4.58–4.74 (3H, m, 1'-CH on GalNAc×3), 5.25–5.40 (6H, m, 3'-CH on Gal×3, and 4'-CH on Gal×3), 6.26–6.40 (2H, m, NH×2), 6.80 (1H, d, J=7 Hz, NH—CH), 7.39 (1H, d, J=7 Hz, NH—CH), 7.94 (1H, m, NH)

Example 14
Synthesis of Phosphoroamidite (5)

116 mg (0.10 mmol) of the compound of Example 9 were dissolved in 5 ml of dry methylene chloride, and 48 mg (0.16 mmol) of 2-cyanoethyl-N,N,N',N'-tetraisopropyl-phosphoroamidite were added while stirring on an ice-ethanol bath under an argon gas flow. 0.28 ml of a 0.5 M 1H-tetrazole-acetonitrile solution was added dropwise at −5 to −10° C. After stirring at room temperature for 3 hours, 5 ml of a cooled 1 M aqueous triethyl ammonium hydrogencarbonate solution were added, and the admixture was further stirred for 10 minutes. The organic layer was isolated, washed consecutively with a 1 M aqueous triethyl ammonium hydrogencarbonate solution and an aqueous saturated sodium chloride solution, dried on anhydrous magnesium sulphate, and concentrated under vacuum. The resulting residue was washed with dry hexane and dried under vacuum to obtain 232 mg of phosphoroamidite as a white viscous substance.

Reference Example 2
Synthesis of Phosphoroamidite (6)

73 mg (0.13 mmol) of the compound of Reference Example 1 were dissolved in 5 ml of dry methylene chloride, and 63 mg (0.21 mmol) of 2-cyanoethyl-N,N,N',N'-tetraisopropyl-phosphoroamidite were added while stirring on an ice-ethanol bath under an argon gas flow. 0.36 ml of a 0.5 M 1H-tetrazole-acetonitrile solution was added dropwise at −5 to −10° C. After stirring at room temperature for 3 hours, 5 ml of a cooled 1 M aqueous triethyl ammonium hydrogencarbonate solution were added, and the admixture was further stirred for 10 minutes. The organic layer was isolated, washed consecutively with a 1 M aqueous triethyl ammonium hydrogencarbonate solution and an aqueous saturated sodium chloride solution, dried on magnesium sulphate, and concentrated under vacuum. The resulting residue was washed with dry hexane and dried under vacuum to obtain 98 mg of phosphoroamidite as a white viscous substance.

$^1$H-NMR (CDCl$_3$) δ: 6.50–6.46 (1H, m, NHCO), 5.39 (1H, brs, Gal-4), 5.22–5.18 (1H, m, Gal-2), 5.04–5.00 (1H, m, Gal-3), 4.56 (1H, d, J=7.5 Hz, Gal-1), 4.32–4.31 (1H, m, Gal-OCH$_2$×½), 4.21–4.11 (2H, m, Gal-6), 3.99–3.87 (2H, m, Gal-5, Gal-OCH$_2$×½), 3.75–3.55 (12H, m, etyleneglycol moiety, NCH(CH$_3$)$_2$×2, CH$_2$CH$_2$CN), 2.67–2.66 (2H, m, CH$_2$CN), 2.35–2.30 (2H, m, CH$_2$CONH), 2.16, 2.06, 2.05, 1.99 (each 3H, s, acetyl), 1.97–1.95 (2H, m, CH$_2$CH$_2$CONH, CH$_2$OP), 1.50–1.49 (12H, dlike, CH(CH$_3$)$_2$×2)

Reference Example 3
Synthesis of Phosphoroamidite (7)

1-β-(2′-hydroxyethyl)-2,3,4,6-tetra-O-acetyl-galactose (280 mg, 0.71 mmol) was dissolved in dry dichloromethane (10 ml), a 0.5 M tetrazole/acetonitrile solution (1.4 ml) was added under an argon atmosphere, a phosphorylation reagent (350 μl, 1.1 mmol) was added, and the admixture was stirred at room temperature for 2 hours. The reaction solution was poured into a 0.5 M aqueous TEAB solution (50 ml) and extracted with dichloromethane. The organic layer was dried on magnesium sulphate, and the solvents were removed by distillation to obtain the phosphoroamidite.

Yield: quantitative. $^1$H-NMR(CDCl$_3$) δ: 5.39 (1H, d, J$_{3,4}$=3.5 Hz, H-4), 5.20 (1H, ddd, J$_{3,4}$=4.0 Hz, J$_{2,3}$=8.0 Hz, J=11.0 Hz, H-2), 5.02 (1H, ddd, J$_{3,4}$=3.5 Hz, J$_{2,3}$=7.0 Hz, J=14.0 Hz, H-3), 4.59 (1H, dd, J$_{1,2}$=8.0 Hz, J=11.0 Hz, H-1), 4.10–4.20 (3H, m), 3.70–4.00 (6H, m), 3.59–3.62 (2H, m), 2.63–2.67 (2H, m), 2.15 (3H, s, OAc), 2.05 (3H, s, OAc), 2.05 (3H, s, OAc), 1.99 (3H, s, OAc), 1.17–1.20 (12H, m)

Structural details of each of the compounds of Examples 1 to 14 in relation to formula (I) are shown in Table 2.

In Table 2, Gal represents galactose, Glc represents glucose and GalNAc represents N-acetyl-galactosamine (same in Table 3 hereinafter). Y in group (II) is diisopropyl amino group.

In compounds in which T$^2$ is group (IV), structures of group (VI) are as follows:

TABLE 3

| | | | Group (IV) | | | | |
|---|---|---|---|---|---|---|---|
| Example | p* | T$^3$* | T$^1$* | q* | T$^4$* | T$^{1**}$ | F$^3$ |
| 2 | 0 | —CONH— | t = 2 | 2 | —CONH— | t = 2 | Gal |
| 3 | 0 | —CONH— | t = 2 | 2 | —CONH— | t = 2 | Glc |
| 4 | 0 | —CONH— | s = 6 | 2 | —CONH— | s = 6 | Gal |
| 5 | 0 | —CONH— | s = 2 | 2 | —CONH— | s = 2 | Gal |
| 6 | 0 | —CONH— | s = 2 | 2 | —CONH— | s = 2 | Gal |
| 7 | 0 | —CONH— | t = 2 | 2 | —CONH— | t = 2 | Gal |
| 8 | 0 | —CONH— | s = 8 | 2 | —CONH— | s = 8 | GalNAc |
| 10 | 0 | —CONH— | s = 6 | 2 | —CONH— | s = 6 | Gal |
| 11 | 0 | —CONH— | s = 2 | 2 | —CONH— | s = 2 | Gal |
| 12 | 0 | —CONH— | t = 2 | 2 | —CONH— | t = 2 | Gal |
| 13 | 0 | —CONH— | s = 8 | 2 | —CONH— | s = 8 | GalNAc |

Example 15
Synthesis of Nucleotide Derivative (1) (1) Synthesis of Tetrathymidine Nucleotide Using an automated DNA synthesizer (Cyclone Plus Nucleic Acid Synthesizer, a product of Milipore), tetrathymidine nucleotide was synthesized on a synthesizing column (15 μmol synthesis scale) according to the β-cyanoethylphosphoroamidite method. Peaction programs and synthesizing reagents provided by or purchased from Milipore were used without alteration.

After completion of the reaction, the column was washed with 10 ml of purified water, the carrier was removed from the column, 5 ml of concentrated aqueous ammonia (25%) was added, and the admixture was allowed to stand at room temperature for 24 hours. The carrier was removed by decantation, the supernatant was concentrated under vacuum, and the resulting supernatant was concentrated under vacuum, 0.7 ml of 100 mM TEAA (pH 8.0) was added to the residue. After filtration, purification was carried out using HPLC under the following conditions:

TABLE 2

| | | | | | Compounds of Example 1–14 | | | | | | |
|---|---|---|---|---|---|---|---|---|---|---|---|
| Example | X | m | (T$^5$)r | n | p | T$^3$ | T$^1$ | F$^1$ | q | T$^4$ | T$^2$ | F$^2$ |
| 1 | benzyloxy | 0 | —CONH— | 0 | 0 | —CONH— | t = 2 | Gal | 2 | —CONH— | t = 2 | Gal |
| 2 | t-butoxy | 0 | —CONH— | 0 | 0 | —CONH— | t = 2 | Gal | 2 | —CONH— | group(IV) | Gal |
| 3 | t-butoxy | 0 | —CONH— | 0 | 0 | —CONH— | t = 2 | Glc | 2 | —CONH— | group(IV) | Glc |
| 4 | HC | 9 | —CONH— | 0 | 0 | —CONH— | s = 6 | Gal | 2 | —CCNH— | group(IV) | Gal |
| 5 | HO | 9 | —CONH— | 0 | 0 | —CONH— | s = 2 | Gal | 2 | —CONH— | group(IV) | Gal |
| 6 | HO | 3 | —CONH— | 0 | 0 | —CONH— | s = 2 | Gal | 2 | —CONH— | group(IV) | Gal |
| 7 | HQ | 3 | —CONH— | 0 | 0 | —CONH— | t = 2 | Gal | 2 | —CONH— | group(IV) | Gal |
| 8 | HO | 9 | —CONH— | 0 | 0 | —CONH— | s = 8 | GalNAC | 2 | —CONH— | group(IV) | GalNAC |
| 9 | HO | 3 | —CONH— | 0 | 0 | —CONH— | t = 2 | Gal | 2 | —CONH— | t = 2 | Gal |
| 10 | group(II) | 9 | —CONH— | 0 | 0 | —CONH— | s = 6 | Gal | 2 | —CONH— | group(IV) | Gal |
| 11 | group(II) | 9 | —CONH— | 0 | 0 | —CONH— | s = 2 | Gal | 2 | —CONH— | group(IV) | Gal |
| 12 | group(II) | 3 | —CONH— | 0 | 0 | —CONH— | t = 2 | Gal | 2 | —CONH— | group(IV) | Gal |
| 13 | group(II) | 9 | —CONH— | 0 | 0 | —CONH— | s = 8 | GalNAC | 2 | —CONH— | group(IV) | GalNAc |
| 14 | group(II) | 3 | —CONH— | 0 | 0 | —CONH— | t = 2 | Gal | 2 | —CONH— | t = 2 | Gal |

[Conditions for HPLC]
Column: ODS-packed column (ODS-2 column, 250×6 mm, a product of G.L. Science) Column temperature: 30° C.
Detection: OD (260 nm)
Flow rate: 1.5 ml/min
Sample volume: 250 μl
Moving phase A: 100 mM TEAA (pH 6.1)
Moving phase B: 95% acetonitrile
0 minute: A:B=95:5; 40 minutes: A:B=80:20; linear gradient
Moving phases which were eluted in a designated retention time were pooled.
Retention time: 25.0–26.0 minutes (1 minute)

A pooled fraction of moving phases was dried under vacuum. The residue was dissolved in 1 ml of 100 mM TEAA, and the solution was added to an ODS column (Sep-Pak Plus, a product of Milipore) equilibrated with 100 mM TEAA containing 10% acetonitrile.

The column was washed with the solution used for equilibration (5 ml×3) and then with purified water (5 ml×3), and eluted with 70% acetonitrile. The eluate was dried under vacuum to obtain a white amorphous powder.

Yield: 27.0% NMR (500 MHz, in $D_2O$): $\delta^{TMS}$=1.87, 1.88, 1.89 (total 12H, each singlet, $CH_3$ on Thymine), 2.28–2.37 (4H, m, 2'-$CH_2$×4×½), 2.48–2.56 (4H, m, 2'-$CH_2$×4×½), 3.79 (1H, dd, J=4 and 12 Hz, 5'-terminal 5'-$CH_2$×½), 3.82 (1H, dd, J=4 and 12 Hz, 5'-terminal 5'-$CH_2$×½), 4.04–4.20 (8H, m), 4.28–4.34 (2H, m), 4'-CH×4 and 5'-$CH_2$×3, 4.58 (1H, q, J=4 Hz, 3'-terminal 3'-CH), 4.83–4.92 (3H, m, 3'-CH×3), 6.20 (1H, dd, J=6.5 and 7 Hz, 1'-CH), 6.23–6.32 (3H, m, 1'-CH×3), 7.64 (1H, s, CH on Thymine), 7.66 (1H, s, CH on Tyhmine), 7.68 (1H, s, CH on Thymine), 7.69 (1H, s, CH on Thymine); FAB-MS:m⁺/z=1177(M–H⁺)

(2) Synthesis of Ethoxy-β-galactose-modified Tetrathymidine Nucleotide

The galactose derivative of phosphoroamidite (Reference Example 3) was dissolved in acetonitrile to a concentration of 60 mM, and the solution was immediately applied onto an automated DNA synthesizer. It was then reacted with tetrathymidine nucleotide previously synthesized on a column for synthesis (15 μmol synthesis scale) according to the β-cyanoethylphosphoroamidite method. After completion of the reaction, a white amorphous powder was obtained in the same manner as described in (1).

Conditions for HPLC were the same as described in (1). The retention time for the pooled fraction was 20.5–21.5 minutes (for 1 minute).

Yield: 39.8% NMR (500 MHz, in $D_2O$): $\delta^{TMS}$=1.89 (6H, s, $CH_3$ on Thymine×2), 1.91 (3H, s, $CH_3$ on Thymine), 1.92 (3H, s, $CH_3$ on Thymine), 2.28–2.40 (4H, m, 2'-$CH_2$×4×½), 2.48–2.57 (4H, m, 2'-$CH_2$×4×½), 3.54 (1H, dd, J=8 and 9 Hz, 2"-CH on Gal), 3.63–3.90 (4H, m, 3"-CH, 5"-CH, 6"-$CH_2$ on Gal), 3.92 (1H, m, 4"-CH on Gal), 4.02–4.20 (10H m), 4.29–4.39 (2H, m), 4'-CH×4 and 5'-$CH_2$×4, 4.44 (1H, d, J=8 Hz, 1"-CH on Gal), 4.57–4.62 (1H, m, 3'-CH), 4.85–4.94 (3H, m, 3'-CH×3), 6.22–6.35 (4H, m, 1'-CH×4), 7.67 (1H, s, CH on Thymine), 7.68 (1H, s, CH on Thymine), 7.71 (1H, s, CH on Thymine), 7.72 (1H, s, CH on Thymine)

Example 16
Synthesis of Nucleotide Derivative (2)
Synthesis of tri(ethoxy-β-galactose)-modified Tetrathymidine Nucleotide The galactose derivative of phosphoroamidite (Example 11) was dissolved in acetonitrile to a concentration of 60 mM, and the solution was immediately applied onto an automated DNA synthesizer. It was then reacted with tetrathymidine nucleotide previously synthesized on a synthesizing column (15 μmol synthesis scale) according to the β-cyanoethylphosphoroamidite method. After completion of the reaction, a white amorphous powder was obtained in the same manner as described in Example 15 (1).

Conditions for HPLC were the same as described in Example 15 (1), except that the moving phase mixing ratios were altered as followed: 0 minute: A:B=95:5; 40 minutes: A:B=70:30; a linear gradient. The retention time for the pooled fraction was 21.5–22.5 minutes (for 1 minute).

Yield: 17.4% NMR (500 MHz, in $D_2O$): $\delta^{TMS}$=1.00–1.25 (10H, m, —$(CH_2)_5$— on decanoyl), 1.48–1.58 (4H, m, —$(CH_2)_2$— on decanoyl), 1.90 (3H, d, J=1 Hz, $CH_3$ on Thymine), 1.91 (3H, d, J=1 Hz, $CH_3$ on Thymine), 1.92 (3H, d, J=1 Hz, $CH_3$ on Thymine), 1.93 (3H, d, J=1 Hz, $CH_3$ on Thymine), 1.97 (2H, m, β$CH_2$ on Glu×2), 2.11 (2H, m, β$CH_2$ on Glu×2), 2.28 (2H, t, J=7 Hz, —$CH_2$CO on decanoyl), 2.20–2.58 (12H, m, 2'-$CH_2$×4 on dRib and γ$CH_2$ on Glu×2), 3.38–3.57 (6H, m, NH$\underline{CH}_2$ on ethylene glycol× 3), 3.54 (3H, m, 2"-CH on Gal×3), 3.64–4.02 (18H, m, O$CH_2$ on ethylene glycol×3, and 3"-CH, 5"-CH, 6"-$CH_2$ on Gal×3), 3.93 (3H, m, 4"-CH on Gal×3), 4.06–4.18 and 4.30–4.40 (12H, m, 4'-CH and 5'-$CH_2$ on dRib×4), 4.24–4.30 (2H, m, αCH on Glu×2), 4.41 (3H, m, 1"-CH on Gal×3), 4.57–4.62 and 4.85–4.94 (4H, m, 3'-CH on dRib×4), 6.25–6.35 (4H, m, 1'-CH on dRib×4), 7.69 (1H, d, J=1 Hz, CH on Thymine), 7.71 (1H, d, J=1 Hz, CH on Thymine), 7.74 (1H, d, J=1 Hz, CH on Thymine), 7.77 (1H, d, J=1 Hz, CH on Thymine)

Example 17
Synthesis of Phosphorothioate Oligodeoxynucleotide Derivative (1)
(1) Synthesis of Tetrathymidine Phosphorothioate Oligodeoxynucleotide A white amorphous powder was obtained in the same manner as described in Example 15 (1), except that, among synthesizing reagents to be used in the automated DNA synthesizer, the oxidizing solution was replaced by Beaucage reagent (a product of Milipore) for thio conversion.

Conditions for HPLC were the same as described in Example 15 (1), except that the moving phase mixing ratios were altered as follows: 0 minute: A:B=85:15; 40 minutes: A:B=75:25; linear gradient. The retention time for the pooled fraction was 8.5–11.5 minutes (for 3 minutes).

Yield: 56.3%. NMR (500 MHz, in $D_2O$): $\delta^{TMS}$=1.88 (3H, s, $CH_3$ on Thymine), 1.94 (9H, s, $CH_3$ on Thymine), 2.27–2.60 (8H, m, 2'-$CH_2$×4), 3.83 (1H, m, 5'-terminal 5'-$CH_2$ on dRib×1/2), 3.86 (1H, m, 5'-terminal 5'-$CH_2$ on dRib×1/2), 4.12–4.27 and 4.36–4.46 (10H m, 4'-CH×4 and 5'-CH, on dRib×3), 4.56–4.62 (1H, m, 3'-terminal 3'-CH on dRib), 4.94–5.14 (3H, m, 3'-CH on dRib×3), 6.22–6.35 (4H, m, 1'-CH×4), 7.66 (1H, m, CH on Thymine), 7.74–7.81 (3H, m, CH on Thymine×3)

(2) Synthesis of tri(ethoxy-β-galactose)-modified Tetrathymidine Phosphorothioate Oligodeoxynucleotide The galactose derivative of phosphoroamidite (Example 11) was dissolved in acetonitrile to a concentration of 70 mM, and the solution was immediately applied onto an automated DNA synthesizer. It was then reacted with tetrathymidine phosphorothioate oligodeoxynucleotide previously synthesized on a column for synthesis (15 μmol synthesis scale) according to the β-cyanoethylphosphoroamidite method. Among synthesizing reagents to be used in the automated DNA synthesizer, the oxidizing solution was replaced by Beaucage reagent for thio conversion. After completion of the reaction, a white amorphous powder was obtained in the same manner as described in Example 15 (1).

Conditions for HPLC were the same as described in (1). The retention time for the pooled fraction was 15.0–21.0 minutes (for 6 minutes).

Yield: 28.5%. NMR (500 MHz, in $D_2O$): $\delta^{TMS}$=1.08–1.25 (10H m, —$(CH_2)_5$— on decanoyl), 1.48–1.62 (4H, m, —(CH$_2$)$_2$— on decanoyl), 1.92–2.02 (14H, m, CH$_3$ on Thymine×4 and βCH$_2$ on Glu), 2.05–2.17 (2H, m, βCH$_2$ on Glu, -CH$_2$CO on decanoyl), 2.20–2.60 (14H, m, —CH$_2$CO on decanoyl, 2'-CH$_2$ on dRib×4 and γCH$_2$ on Glu×2), 3.38–3.57 (6H, m, NCH$_2$ on ethylene glycol×3), 3.54 (3H, dd, J=9 and 9 Hz, 2"-CH on Gal×3), 3.64–4.02 (18H, m, OCH$_2$ on ethylene glycol×3, and 3"-CH, 5"-CH, 6"-CH$_2$ on Gal×3), 3.93 (3H, m, 4"-CH on Gal×3), 4.12–4.28 and 4.42–4.50 (12H, m, 4'-CH and 5'-CH$_2$ on dRib×4), 4.25–4.30 (2H, m, αCH on Glu=2), 4.41 (3H, m, 1"-CH on Gal×3), 4.57–4.63 (4H, m, 3'-CH on 3'-terminal dRib), 5.01–5.28 (3H, m, 3'-CH on dRib×3), 6.27–6.38 (4H, m, 1'-CH on dRib×4), 7.75–7.88 (4H, m, J=1 Hz, CH on Thymine×4)

Example 18

Synthesis of Phosphorothioate Oligodeoxynucleotide Derivative (2)

(1) Synthesis of Phosphorothioate Oligodeoxynucleotide

Using a 1 μmol synthesis scale column, a thio oligonucleotide having a base sequence of 5'-ATGCCCCTCAACGTT-3' (SEQ ID NO.1) was synthesized in the same manner as described in Example 17 (1). The reaction program was completed leaving the DMT group at the 5' terminal intact. The column was washed with 3 ml of purified water, the carrier was removed from the column and allowed to stand at room temperature for 24 hours after adding 2 ml of concentrated aqueous ammonia (25%). After removing the carrier by decantation, 0.4 ml of the reaction mixture was mixed with the same volume of purified water, and then applied on an Olig-Pak column (a product of Milipore) equilibrated with 1 M TEAA (pH 7.0). The column was washed with 3% aqueous ammonia (5 ml×3), purified water (5 ml×3) and then with 5 ml of 2% trifluoroacetic acid to remove the DMT group at the 5' terminal. The column was then washed with purified water (5 ml×2) and then eluted with 40% acetonitrile. The abovementioned column treatment was repeated 5 times. A pooled eluate fraction was dried under vacuum to obtain a white amorphous powder.

Yield: 48.2%.

(2) Synthesis of tri(triethoxy-β-galactose)-modified Thio Oligonucleotide

Using a 1 μmol synthesis scale column, tri(ethoxy-β-galactose)-modified phosphorothioate oligodeoxynucleotide having a base sequence of 5'-ATGCCCCTCAACGTT-3' (SEQ ID NO.1) was synthesized in the same manner as described in Example 17 (2), but using phosphoroamidite of a galactose derivative (Example 12) in the modification reaction. After completion of the reaction, the column was washed with 3 ml of purified water, the carrier was removed from the column and allowed to stand at room temperature for 24 hours after adding 2 ml of concentrated aqueous ammonia (25%). After removing the carrier by decantation, the reaction mixture was gel-filtrated on a Sephadex G-25 column (NAPS-25 column, a product of Pharmacia; bed volume: 9 ml) equilibrated with 100 mM phosphate buffer (pH 7.4) and the solvents were replaced by phosphate buffer. The first eluate (3 ml) was discarded and the following eluate (3 ml) was collected to obtain a crude fraction.

In order to isolate a nucleotide with a bonded galactose derivative, an agarose column (bed volume: 10 ml, equilibrated with 100 mM phosphate buffer) immobilized with a galactose bondable lectin, RCA 120, was used. The crude fraction was applied on the abovementioned column and an unbound fraction was eluted with 20 ml of 100 mM phosphate buffer. Next, a lectin-bound fraction was eluted with 20 ml of 100 mM phosphate buffer containing 0.2 M galactose and collected. In order to remove galactose in the fraction, the following procedure was carried out using an ODS column (Sep-Pak Plus).

One tenth volume of 1 M TEAA was added to the lectin-bound fraction, and the admixture was applied on an ODS column (Sep-Pak Plus) equilibrated with 100 mM TEAA containing 10% acetonitrile. The ODS column was washed with 10 ml of the buffer used for equilibration, and then further with 10 ml of purified water. Next, elution was carried out with 70% acetonitrile and the eluate was dried under vacuum to obtain a white amorphous powder.

Yield: 42.8%.

Example 19

Synthesis of Phosphorothioate Oligodeoxynucleotide Derivative (3)

(1) Synthesis of Phosphorothioate Oligodeoxynucleotide

Using a 1 μmol synthesis scale column, a thio oligonucleotide having a base sequence of 5'-AACGTTGAGGGGCAT-3' (SEQ ID NO.2) was synthesized in the same manner as described in Example 18 (1). A white amorphous powder was obtained.

Yield: 65.3%.

(2) Synthesis of tri(triethoxy-β-galactose)-modified Thio Oligonucleotide

Using a 1 μmol synthesis scale column, tri(triethoxy-β-galactose)-modified thio phosphorothioate oligodeoxynucleotide having a base sequence of 5'-AACGTTGAGGGGCAT-3' (SEQ ID NO.2) was synthesized in the same manner as described in Example 18 (2). Phosphoroamidite (Example 12) was used in the modification reaction. A white amorphous powder was obtained.

Yield: 31.5%.

Example 20

Synthesis of Phosphorothioate Oligodeoxynucleotide Derivative (4)

(1) Synthesis of Phosphorothioate Oligodeoxynucleotide

Using a 1 μmol synthesis scale column, a thio oligonucleotide having a base sequence of 5'-GGACTCAGACTCGCGTCC-3' (SEQ ID NO.3) was synthesized in the same manner as described in Example 18 (1). A white amorphous powder was obtained.

Yield: 62.8%.

(2) Synthesis of tri(triethoxy-β-galactose)-modified Thio Oligonucleotide

Using a 15 μmol synthesis scale column, tri(triethoxy-β-galactose)-modified phosphorothioate oligodeoxynucleotide having a base sequence of 5'-GGACTCAGACTCGCGTCC-3' (SEQ ID NO.3) was synthesized in the same manner as described in Example 17 (2), but using phosphoroamidite of a galactose derivative (Example 12) in the modification reaction. After completion of the reaction, the column was washed with 10 ml of purified water, the carrier was removed from the column and allowed to stand at room temperature for 24 hours after adding 10 ml of concentrated aqueous ammonia (25%). After removing the carrier by decantation, 2 ml of the reaction mixture were gel-filtrated on an NAPS-25 column equilibrated with 100 mM phosphate buffer, and the solvents were replaced by phosphate buffer. The first eluate (3 ml) was discarded and the following eluate (3 ml) was collected. The abovementioned gel filtration was repeated 5 times to obtain a crude fraction.

The crude fraction was applied on an agarose column (bed volume: 100 ml, equilibrated with 100 mM phosphate buffer) immobilized with a galactose bondable lectin, RCA 120, and an unbound fraction was removed by eluting with 300 ml of 100 mM phosphate buffer. Next, a lectin-bound fraction was eluted with 300 ml of 100 mM phosphate buffer containing 0.2 M galactose and collected. One tenth volume of 1 M TEAA was added, and the admixture was applied on an ODS column (Sep-Pak Plus) equilibrated with 100 mM TEAA containing 10% acetonitrile. The ODS column was washed with 10 ml of the buffer used for equilibration, and then further with 10 ml of purified water. Next, elution was carried out with 70% acetonitrile, and the eluate was dried under vacuum to obtain a white amorphous powder.

Yield: 24.6%.

Compounds of Examples 18 to 20 were analyzed using HPLC to confirm the presence of a single peak only:

[Conditions for HPLC]

Column: Cation exchange column (Waters Gen-Pak Fax, 100×4.6 mm)

Column temperature: 80° C.

Detection: OD at 260 nm

Flow rate: 1.5 ml/min

Sample volume: 20 µl (equivalent to 1 $OD_{260}$)

Moving phase A: 100 mM Tris-HCl (pH 7.0)/30% acetonitrile

Moving phase B: 100 mM Tris-HCl (pH 7.0)/30% acetonitrile/2 M KBr 0 minute: A:B=95:5; 30 minutes: A:B=50:50 (0.1 M→1.0 M KBr linear gradient)

Example 21

Synthesis of Phosphorothioate Oligodeoxynucleotide Derivative (5)

Synthesis of di(triethoxy-β-galactose)-modified Thio Oligonucleotide

Using a 1 µmol synthesis scale column, di(triethoxy-β-galactose)-modified phosphorothioate oligodeoxynucleotide having a base sequence of 5'-AACGTTGAGGGGCAT-3' (SEQ ID NO.2) was synthesized in the same manner as described in Example 18 (2). A galactose derivative, phosphoroamidite (Example 14), was used in the modification reaction. A white amorphous powder was obtained.

Yield: 21.2%.

Example 22

Synthesis of Phosphorothioate Oligodeoxynucleotide Derivative (6)

Synthesis of triethoxy-β-galactose-modified Phosphorothioate Oligodeoxynucleotide Using a 1 µmol synthesis scale column, triethoxy-β-galactose-modified thio oligonucleotide having a base sequence of 5'-AACGTTGAGGGGCAT-3' (SEQ ID NO.2) was synthesized in the same manner as described in Example 18 (2). A galactose derivative, phosphoroamidite (Reference Example 2), was used in the modification reaction. A white amorphous powder was obtained.

Yield: 6.23%.

Protein Expression Suppression Test (1)

HepG2 cells were inoculated on a 6-well microplate (1×10$^6$ per well) and incubated for 5 days to get nearly confluent growth. Each well was washed with fresh RPMI1640 medium, after which 2 ml of the same medium was added. Further, 50 µl of PBS(−) containing the compounds of the present invention at various concentrations were added, and incubation was carried out for 24 hours. Next, wells were washed with RPMI1640 medium with no L-methionine, after which 30 µCi of [$^{35}$S] L-methionine per well were added, and incubation was carried out for 20 hours. After washing with ice-cold PBS(−), the cells were scraped using a scraper and collected by centrifugation.

The following procedures were all conducted at 4° C. After addition of 0.2 ml of lysis buffer (20 mM Tris-HCl (pH 7.4)/1 mM EDTA/1 mM PMSF/0.3% Nonidet P-40), the collected cells were dissolved by pipetting, and the supernatant was obtained by centrifugation. After addition of 0.3 ml of 20 mM Tris-HCl (pH 7.4)/150 mM NaCl and 1 pg of monoclonal human c-myc antibody (Clone 9E10, Catalogue # OP10, a product of Oncogene Science), the supernatant was allowed to stand in ice for 1 hour. Next, 0.1 ml of Protein A-Sepharose gel was added and the admixture was shaken for 1 hour. The gel was then washed 3 times with 1 ml of 20 mM Tris-HCL (pH 7.4)/150 mM NaCl. After the addition of 100 µl of 0.1 M citric acid (pH 2.0), the gel was allowed to stand for 10 minutes. Next, 50 µl of the resultant supernatant were mixed with the same volume of SDS-PAGE sample buffer and heated in a boiling water bath for 3 minutes to obtain a sample for SDS-PAGE. The sample (10 µl per well) was applied on a 8% SDS-PAGE (a product of TEFCO) and electrophoresis was carried out at 40 mA for 1 hour. After fixing with 7% acetic acid and 20% methanol, the gel was dried at 60° C. for 1 hour. [$^{35}$S] c-myc protein band was detected by exposing the gel to X-ray film (Hyperfilm β max, a product of Amersham).

Figure 1:
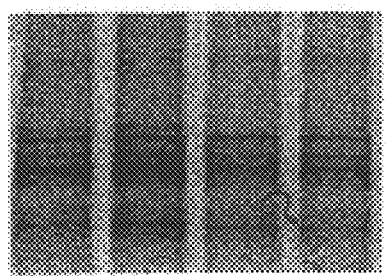
FIG. 1 shows the inhibitory effect of the compounds of the present invention on expression of c-myc protein in HepG2 cells. Lanes 1, 2, 3 and 4 are with compounds of Example 19 (1), Example 22, Example 21 and Example 19 (2), respectively. In all cases, the compounds were added at a concentration of 1.00 μM.
Figure 2:
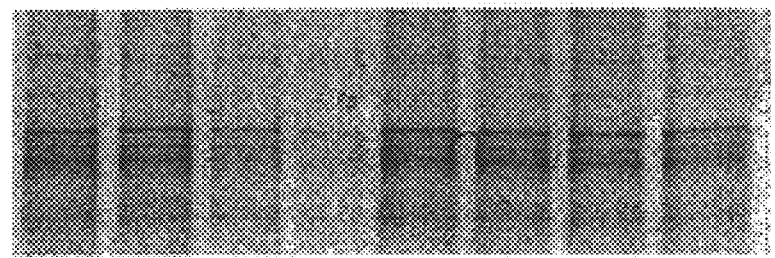
FIG. 2 shows the inhibitory effect of the compounds of the present invention on expression of c-my protein in HepG2 cells.

Results are shown in FIG. 1. When the compounds of Examples 19 (1), 19 (2), 21 and 22 were added to the medium at a concentration of 1 µM, there was no difference in the amount of expressed c-myc protein between the compound of Example 19 (1) having no galactose residue and the compound of Example 22 having 1 galactose residue. On the other hand, expression of c-myc protein was suppressed as the number of galactose residues increased in the compounds of Examples 22 and 19 (2). When the compound of Example 19 (2) having 3 galactose residues and the unmodified compound of Example 19 (1) were added at a concentration between 0.04 to 1.0 µM, suppression of synthesis was not observed with the compound of Example 19 (1), but concentration-depending suppression of synthesis was observed with the compound of Example 19 (2) (FIG. 2).

Protein Expression Suppression Test (2)

Suppression of expression of epidermal cell growth factor receptor protein was tested as follows:

(1) Preparation of Rat Culture Hepatocytes

Under anesthesia with Nembutal, cannulas were inserted into the portal vein of male Wister rats (6 weeks of age). Perfusion from the portal vein was carried out using Hanks' buffer (containing 0.2 g/L EGTA, $Ca^{2+}$, or $Mg^{2+}$ free) heated to 37° C. at a flow rate of 20 ml/min for 10 minutes to bleed the liver. Next, perfusion was carried out using Hanks' buffer containing 0.5 g/L collagenase for 10 minutes, after which the liver was shaken in ice-cooled Eagle's Minimum Essential Medium to disperse the cells.

After filtration through gauze, hepatocytes were purified by centrifugation and that survivability was more than 90% was confirmed by Trypan Blue staining. The hepatocytes were suspended in Dulbecco's Minimum Essential Medium containing 10% fetal calf serum, and the cell suspension was inoculated into a collagen-coated 6-well microplate at 10,000,000 cells/well. The plate was incubated in a 5% $CO_2$ atmosphere at 37° C. for 2 hours. After washing the wells with medium to remove unabsorbed cells, fresh medium was added, and incubation was further continued for 22 hours.

(2) Induction of Epidermal Growth Factor Receptor (EGFR) Down Regulation

Each well was washed with a test medium (Williams' Medium E containing 10 nM insulin, 10 nM dexamethasone and 0.5% bovine serum albumin), and 1.5 ml of the test medium was added. 100 µl of epidermal growth factor (10 µg/ml) were added to each well, and incubation was carried out for 6 hours.

(3) Addition of Oligodeoxynucleotide

After washing with the test medium, the test medium containing the compounds of Example 20 (1) or (2) was added at various concentrations, and incubation was carried out for 18 hours.

(4) Measurement of Specific Uptake of EGF via EGFR

The wells were washed with the test medium, fresh test medium was added to the wells, then 0.1 mCi of [$^{125}$I] EGF (a product of Amersham) was added to each well, and incubation was carried out for 1 hour. 1 ml of 1 N NaOH was added to each well to dissolve the cells, after which a 0.1 ml portion was sampled to determine the protein concentration. Another portion of 0.8 ml was sampled to measure radio activity to calculate the EGF uptake per unit hepatocyte protein. At the same time, [$^{125}$I] EGF uptake with the addition of an excessive amount of unlabeled EGF (1.5 µg/well) was measured. The specific EGF uptake via EGF receptor was calculated by subtracting this value.

(5) Results

The amounts of EGF-specific binding in rat culture hepatocytes treated by different procedures are shown in FIG. 3. "Negative control" means that step (4) was carried out after step (2) omitting step (3), in which the value represents the EGF-specific bonding immediately after EGFR down regulation was induced. "Positive control" means that the amount of EGF-specific binding was obtained by the same procedure, but with no addition of EGF. "+EGF, Non AON" means that step (3) was carried out using the test medium without the compound of Example 20 (1) or (2), and "Non-treatment" means that steps (2) and (3) were carried out with no addition of EGF nor the compound of Example 20 (1) or (2), in which the level of binding was about the same as that of the positive control. When step (3) was carried out with the addition of the compound of Example 20 (1) in the indicated concentrations, the amounts of binding at the concentrations of 0.316 µM or less were about the same as that for the positive control. When step (3) was carried out with addition of the compound of Example 20 (2) at the indicated concentrations, the amount of EGF-specific binding decreased depending on the amounts of compound.

Growth Suppression Test

HepG2 cells were suspended in RPMI1640 medium containing 10% fetal calf serum and inoculated on a 96-well microplate (1000 cells per well), and the plate was incubated at 37° C. for 2 days under a 5% $CO_2$ atmosphere. Each well was washed with Dulbecco's phosphate-buffered saline with $Ca^{2+}$, or $Mg^{2+}$ free (PBS(-)), and then 100 µl of DM-160 medium containing 0.5% BSA and the compounds of the present invention at various concentrations were added to each well. After incubation for 48 hours, the wells were washed again with PBS (-), the free medium containing of the compounds of the same concentrations and fresh medium were added to each well, and incubation was carried out for another 48 hours. Each well was washed with PBS(-), 100 µl of Dulbecco's Minimum Essential Medium without phenol red and 10 µl of a cell counting reagent (a product of Wako Pure Chemicals) were added, and then incubation was carried out for 3 hours. Absorption at 450 nm was measured for each well using a microplate reader to calculate the number of viable cells. Results are shown in FIG. 4.

The compounds of Examples 19 (1) and 18 (1) had no effect in cell growth suppression at all given concentrations. In contrast, the compounds of Examples 19 (2) and 18 (2) in which a derivative having 3 galactose residues showed an improvement in suppressing cell growth. In particular, the compound of Example 19 (2) inhibited the growth at a concentration of about 1 µM, in which suppressive activity was enhanced at least 7 times by the introduction of the galactose derivative.

We claim:

1. A compound of general formula (I):

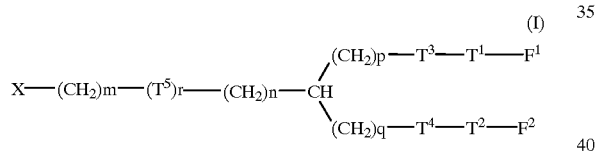

in which

X is group (II):

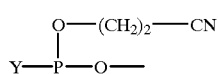

(in which Y is a leaving group) or group (III):

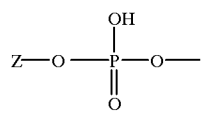

(in which Z is an oligonucleotide or a nucleotide derivative in which one or two of the oxygen atoms at a phosphoric ester bonding site are substituted by other atoms or groups as shown by the following formula:

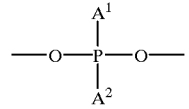

wherein $A^1$ and $A^2$ are selected from the following combinations:

| $A^1$ | $A^2$ |
|---|---|
| —OH | =O |
| =O | —CH$_3$ |
| —OH | =S |
| —SH | =S |
| =O | —O-Alkyl |
| =S | —CH$_3$ |
| =O | —NH-Alkyl |
| =O | —BH$_3$ |

), $T^1$ is —(CH$_2$)s— (in which s represents an integer between 2 and 10), or (CH$_2$CH$_2$O)t—(CH$_2$)$_2$— (in which t represents an integer between 1 and 3),
$T^2$ is —(CH$_2$)u— (in which u represents an integer between 2 and 10), —(CH$_2$CH$_2$O)v—(CH$_2$)$_2$— (in which v represents an integer between 1 and 3), or group (IV):

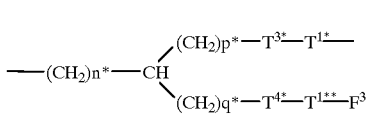

(in which T$^{1*}$ and T$^{1**}$ are each as defined above for T$^1$, and n*, p*, q*, T$^{3*}$, T$^{4*}$ and F$^3$ are each as defined below for n, p, q, T$^3$, T$^4$ and F$^1$, where each group and its asterisk-labeled counterpart can be the same or different), T$^3$, T$^4$ and T$^5$, which may be the same or different, each represent —CONH—, —NHCO— or —O—, provided that when either one of T$^3$, T$^4$ and T$^5$ represents —O—, other two groups represent a group other than —O—, F$^1$ and F$^2$, which may be the same or different, each represent a monosaccharide selected from the group consisting of galactose, glucose and galactosamine, or a derivative thereof, or a disaccharide consisting of the monosaccharide and/or the derivative thereof, wherein a hydroxyl group(s) which does not participate in any reactions in the monosaccharide, the derivative thereof and the disaccharide can be protected, and a hydroxyl (group(s) which does not participate in any reactions in the monosaccharide, the derivative thereof, and the disaccharide can be protected, m represents an integer between 0 and 10,
n represents an integer between 0 and 4,
p represents an integer between 0 and 4,
q represents an integer between 0 and 4 and
r represents an integer 0 or 1.

2. The compound according to claim 1, wherein s represents an integer between 2 and 8,
t represents 2,
v represents 2,
T$^3$, T$^4$ and T$^5$ represent —CONH—,
F$^1$ and F$^2$, which may be the same or different, each represent galactose, galactosamine, N-acetylgalactosamine, lactose, lactosamine or N-acetyllactosamine,
m represents an integer 0 or between 2 and 10,
n represents an integer 0, 1 or 2.
P represents an integer 0, 1 or 2,
q represents an integer 0, 1 or 2, and
r represents an integer 1.

3. A compound of general formula (1a):

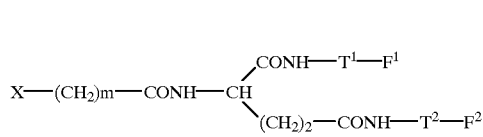

(Ia)

in which
X is group (II):

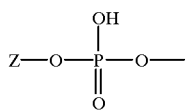

(II)

(in which Y is a leaving group) or group (III)

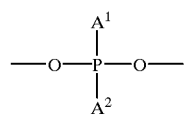

(III)

(in which z is an oligonucleotide or a nucleotide derivative in which one or two of the oxygen atoms at a phosphoric ester bonding site are substituted by other atoms or groups as shown by the following formula:

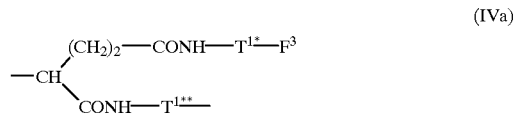

wherein A$^1$ and A$^2$ are selected from the following combinations:

| A$^1$ | A$^2$ |
|---|---|
| —OH | =O |
| =O | —CH$_3$ |
| —OH | =S |
| —SH | =S |
| =O | —O-Alkyl |
| =S | —CH$_3$ |
| =O | —NH-Alkyl |
| =O | —BH$_3$  ), |

T$^1$ is —(CH$_2$)s— (in which s represents an integer between 2 and 8), or —(CH$_2$CH$_2$O)$_2$—(CH$_2$)$_2$—,
T$^2$ is —(CH$_2$)u— (in which u represents an integer between 2 and 8), —(CH$_2$CH$_2$O)$_2$—(CH$_2$)—, or group (IVa):

(IVa)

(in which T$^{1*}$ and T$^{1**}$ are as defined for T$^1$, and F$^3$ is as defined thereinafter for F$^1$, but can be the same as or different from T$^1$ and F$^3$ respectively), F$^1$ and F$^2$, which may be the same or different, each represent a monosaccharide selected from the group consisting of galactose and galactosamine, or a derivative thereof, or a disaccharide consisting of the monosaccharide and/or the derivative thereof, wherein a hydroxyl group(s) which does not participate in any reactions in the monosaccharide, the derivative thereof and the disaccharide can be protected, and m is an integer between 3 and 9.

4. The compound according to claim 3, wherein F$^1$ and F$^2$, which may be the same or different, each represent galactose, galactosamine, N-acetylgalactosamine, lactose, lactosamine or N-acetyllactosamine.

5. The compound according to any one of claims 1 to 4, wherein X represents group (II).

6. The compound according to claim 5, wherein Y represents an diisopropylamino group or a morpholyl group.

7. The compound according to any one of claims 1 to 4, wherein X represents group (III).

8. The compound according to claim 7, wherein Z is selected from the group consisting of an oligodeoxyribonucleotide and an oligoribonucleotide and their phosphorothioate derivatives and methylphosphate derivatives.

9. The compound according to claim 8, wherein Z is an antisense oligonucleotide.

10. The compound according to claim 8, wherein Z is selected from the sequences consisting of SEQ ID Nos: 1,2 and 3.

11. A pharmaceutical composition comprising the compound according to claim 1.

12. The pharmaceutical composition according to claim 11, which is used for a medicament selected from the group consisting of a therapeutic agent for a malignant tumor, an anti-viral agent, an antirheumatic agent, an anti-inflammatory agent, an anti-allergic agent, an immunosuppressive agent, a circulatory function improving agent and an endocrine function improving agent.

13. A method for treating a disorder selected from the group consisting of a malignant tumor, a viral infection, an inflammatory disorder, an allergic disorder, an immune disorder, a circulatory disorder and an endocrine disorder, comprising administrating to an animal including a human the compound according to claim 1.

14. A method for manufacturing a medicament selected from the group consisting of a therapeutic agent for a malignant tumor, an anti-viral agent, an antirheumatic agent, an anti-inflammatory agent, an anti-allergic agent, an immunosuppressive agent, a circulatory function improving agent and an endocrine function improving agent, which comprises admixing the compound of claim 1 with a carrier therefor.

15. A medicament selected from the group consisting of a therapeutic agent for a malignant tumor, an anti-viral agent, an antirheumatic agent, an anti-inflammatory agent, an anti-allergic agent, an immunosuppressive agent, a circulatory function improving agent and an endocrine function improving agent, which comprises the compound of claim 1 and a carrier therefor.

* * * * *